United States Patent [19]
Vanney et al.

[11] Patent Number: 6,007,577
[45] Date of Patent: *Dec. 28, 1999

[54] PROSTHETIC HEART VALVE WITH INCREASED VALVE LUMEN

[75] Inventors: Guy P. Vanney, Blaine; Avrom M. Brendzel, Roseville; James R. Ringdal, Blaine, all of Minn.

[73] Assignee: St. Jude Medical, Inc., St. Paul, Minn.

[ * ] Notice: This patent is subject to a terminal disclaimer.

[21] Appl. No.: 08/937,521

[22] Filed: Sep. 25, 1997

Related U.S. Application Data

[63] Continuation-in-part of application No. 08/664,235, Jun. 7, 1996, which is a continuation-in-part of application No. 08/476,223, Jun. 7, 1995, abandoned.

[51] Int. Cl.⁶ .......................................................... A61F 2/24
[52] U.S. Cl. ...................................................................... 623/2
[58] Field of Search ........................................... 623/2, 900

[56] References Cited

U.S. PATENT DOCUMENTS

| | | |
|---|---|---|
| 3,691,567 | 9/1972 | Cromie . |
| 4,078,268 | 3/1978 | Possis . |
| 4,506,394 | 3/1985 | Bédard . |
| 4,535,483 | 8/1985 | Klawitter et al. ............................ 623/2 |
| 4,597,767 | 7/1986 | Lenkei ........................................ 623/2 |
| 4,705,516 | 11/1987 | Barone et al. .............................. 623/2 |
| 4,743,253 | 5/1988 | Magladry ................................... 623/2 |
| 4,888,009 | 12/1989 | Lederman et al. .......................... 623/2 |
| 4,935,030 | 6/1990 | Alonso ....................................... 623/2 |
| 5,035,709 | 7/1991 | Wieting et al. ............................. 623/2 |
| 5,137,532 | 8/1992 | Bokros et al. .............................. 623/2 |
| 5,336,259 | 8/1994 | Waits et al. ................................. 623/2 |
| 5,360,014 | 11/1994 | Sauter et al. ............................. 128/774 |
| 5,545,216 | 8/1996 | Bokros et al. .............................. 623/2 |
| 5,562,729 | 10/1996 | Purdy et al. ................................ 623/2 |
| 5,824,062 | 10/1998 | Patke et al. ................................. 623/2 |

FOREIGN PATENT DOCUMENTS 1 180 087  10/1964  Germany .

OTHER PUBLICATIONS

"The CarboMedics® "Top Hat" Supraannular Prosthesis in the Small Aortic Root," by S. Roedler et al., *J Card Surg*, vol. 10, pp. 198–204 (1995).
"Theory and Problems of Fluid Dynamics," by W. Hughes et al., *Schaum's Outline Series*, McGraw–Hill Book company, pp. 3–4 and 84 (1967).
"Rationalizing Antithrombotic Management for Patients with Prosthetic Heart Valves," by E. Butchart, *The Journal of Heart Valve Disease*, v.4:pp. 106–113, (1995).
"Prosthetic Valves for the Small Aortic Root," by H. Barner et al., *J Card Surg*, vol. 9, pp. 154–157 (1994).
Brochure entitled: "St. Jude Medical Mechanical Heart Valve Hemodynamic Plus Series" (1995).

*Primary Examiner*—David H. Willse
*Attorney, Agent, or Firm*—Hallie A. Finucane, Esq.; Westman, Champlin & Kelly, P.A.

[57] ABSTRACT

A heart valve prosthesis having a valve housing providing a lumen therethrough. The valve housing has a first annulus on one end and a second annulus on the other end spaced apart from the first annulus. A suture cuff is used for attaching the valve housing to heart tissue of a patient. The cuff is attached between the first annulus and the second annulus. The cuff is positioned such that prosthesis is attached in a supra-annular position relative to a tissue annulus of the heart. The design allows for an increased valve lumen.

19 Claims, 18 Drawing Sheets

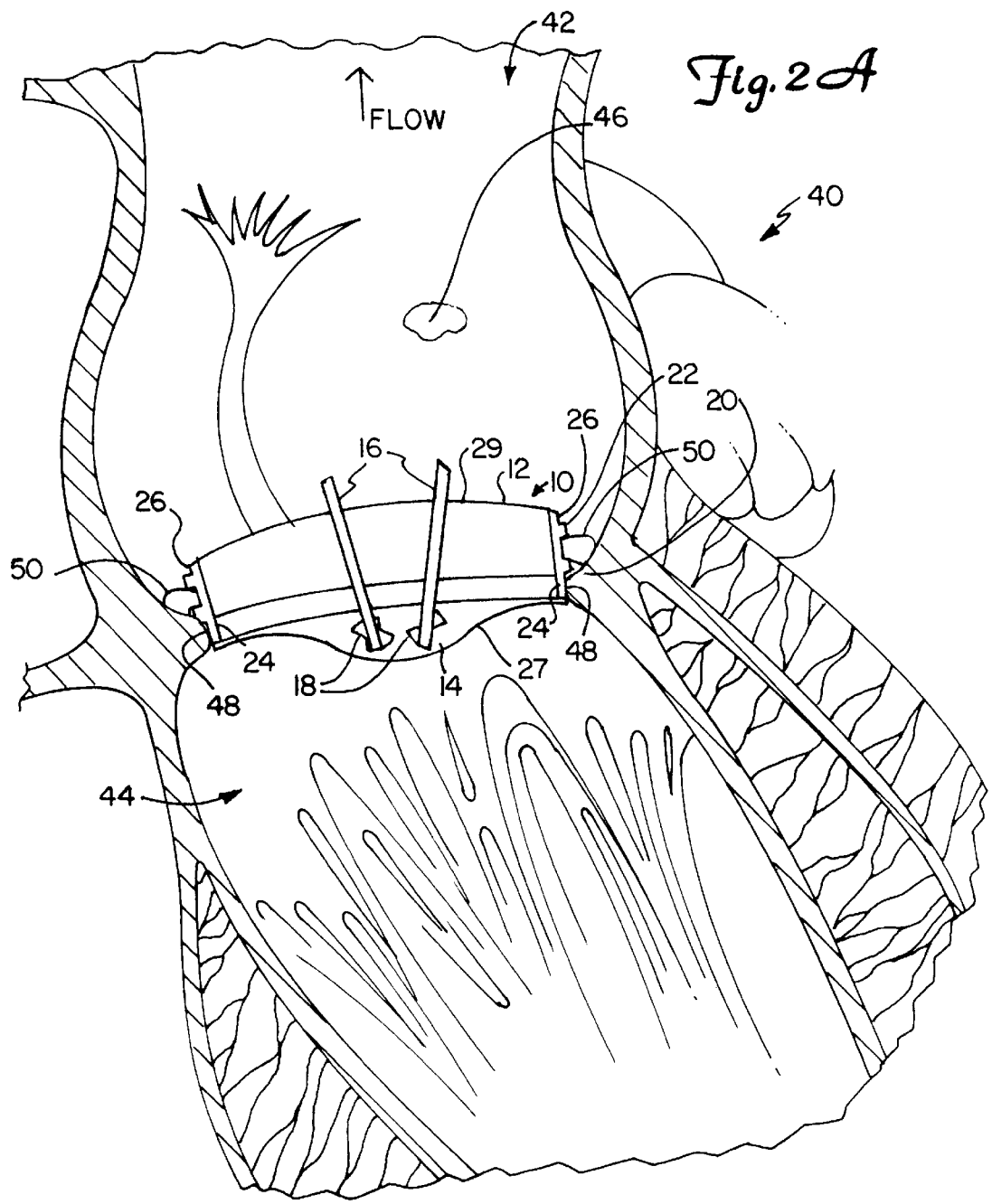

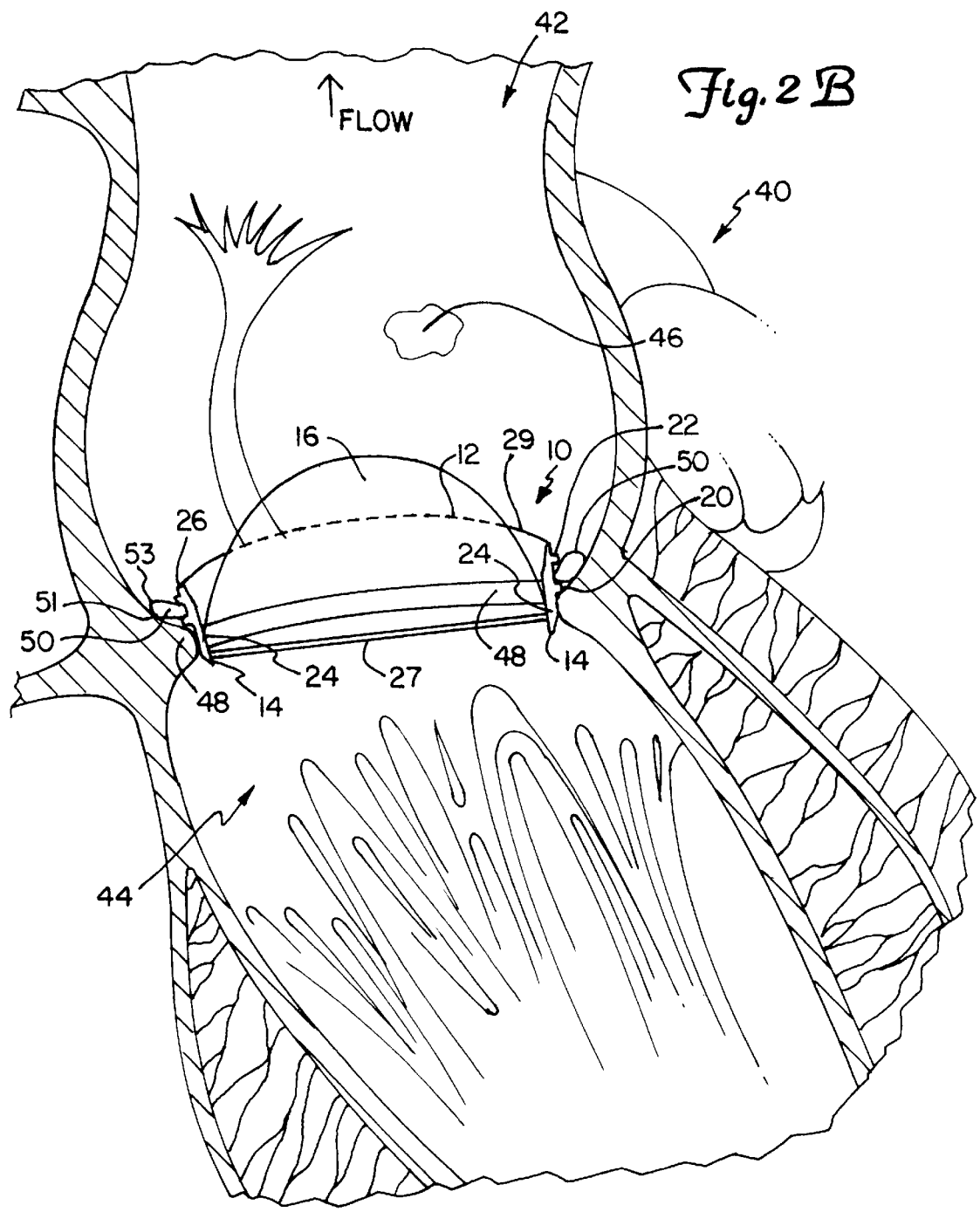

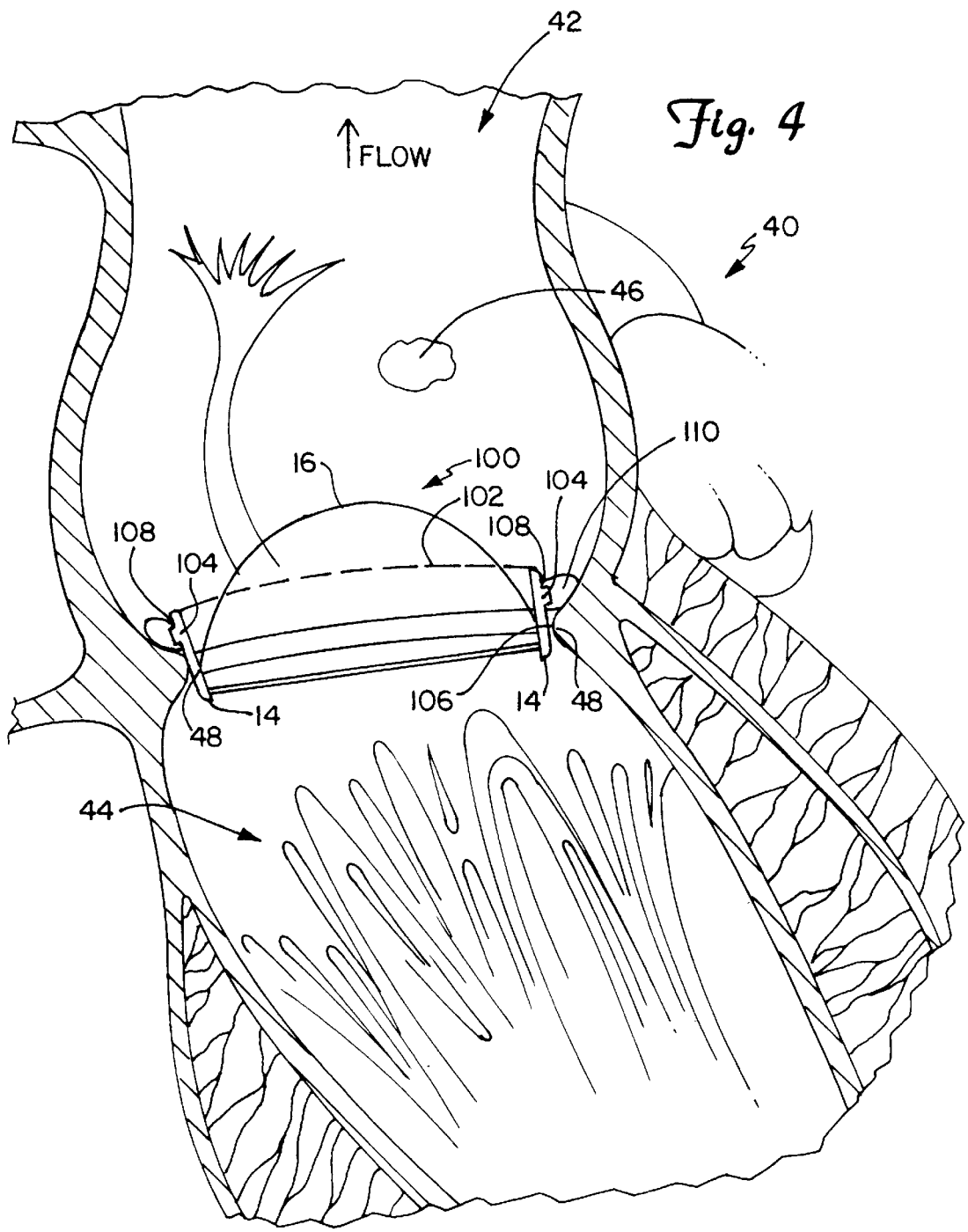

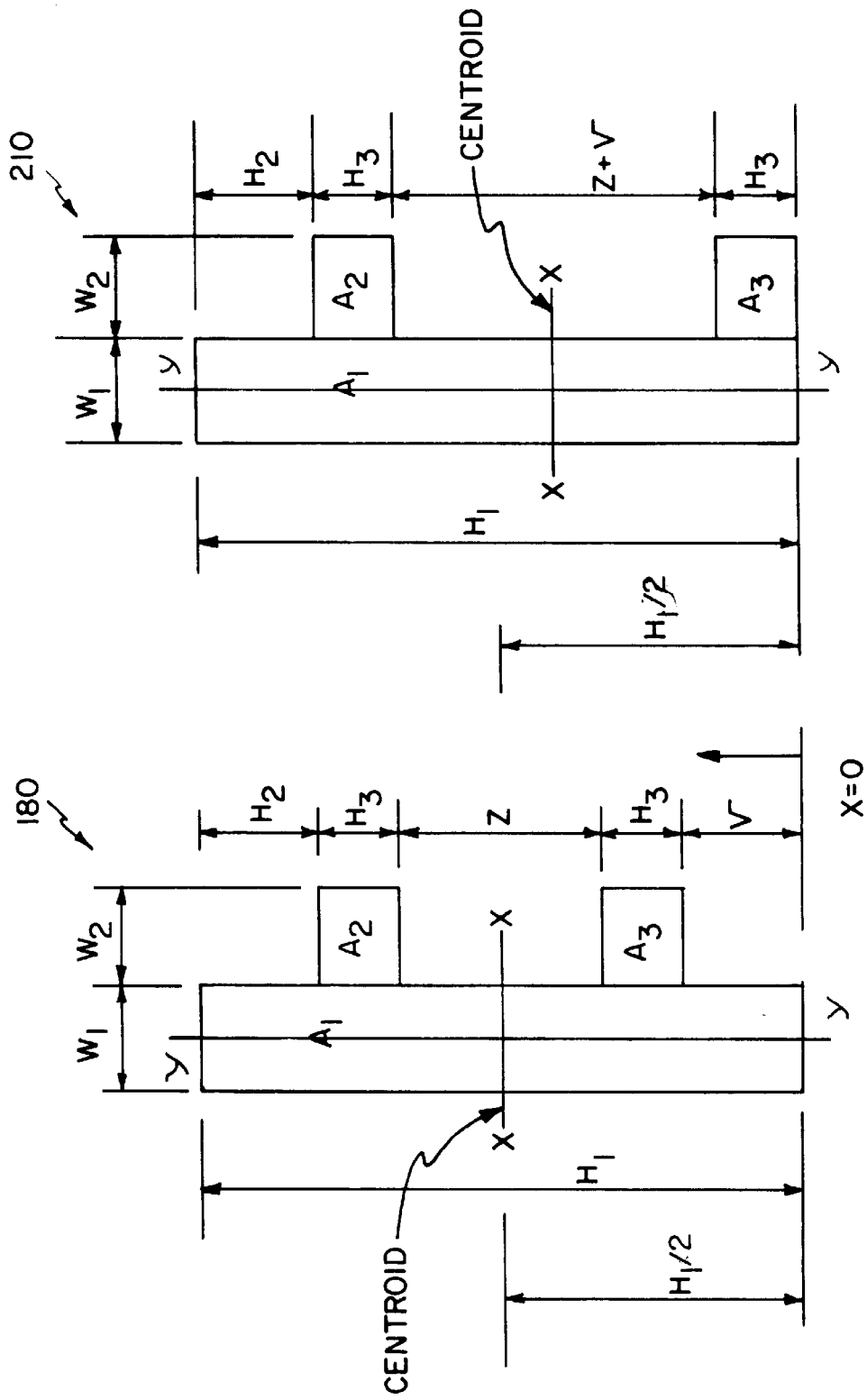

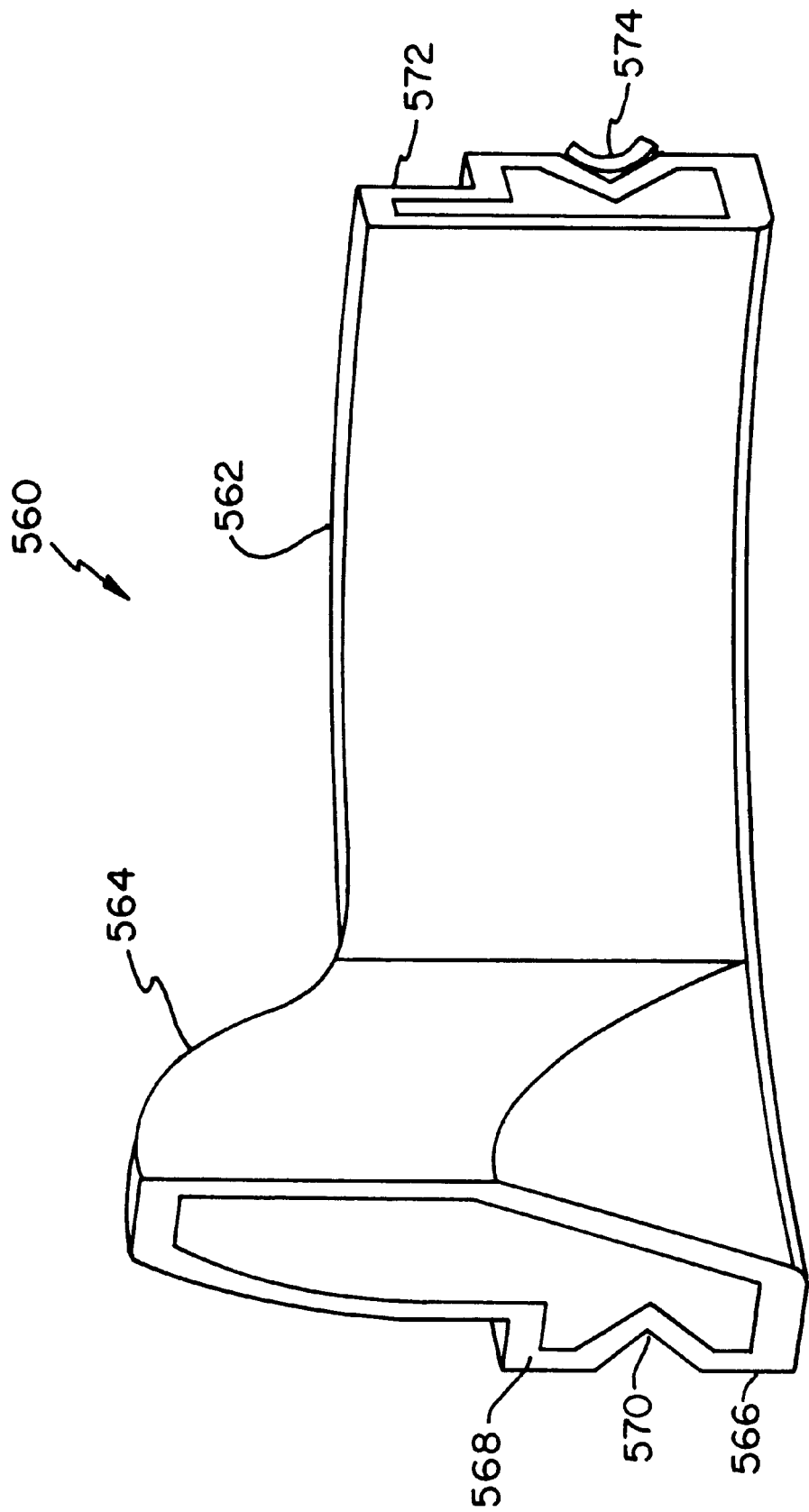

PROSTHETIC HEART VALVE WITH INCREASED VALVE LUMEN

This is a Continuation-In-Part application of U.S. Ser. No. 08/664,235, filed Jun. 7, 1996, pending, which is a Continuation-In-Part application of U.S. Ser. No. 08/476,223, filed on Jun. 7, 1995, now abandoned.

FIELD OF THE INVENTION

The present invention relates to prosthetic heart valves. More particularly, the invention relates to an increased valve lumen of a prosthetic heart valve to improve hemodynamic performance.

BACKGROUND OF THE INVENTION

Prosthetic heart valves are used as a replacement for natural heart valves of patients. A standard implantable mechanical heart valve typically includes an annular valve housing or body (often called an "orifice") to provide a lumen or passageway therethrough for blood flow. One or more occluders mounted to the valve are movable between an open position, allowing blood flow, and a closed position which blocks blood flow. In many mechanical valves, the occluders are essentially plate-like members called "leaflets." Typical configurations include one, two or three leaflets in the valve body.

An attachment mechanism typically surrounds the valve body and is used to secure, typically with sutures, the valve to the patient's heart tissue. While some early prosthetic valves used hooks or barbs for attachment, a fabric suture or sewing cuff which is secured to the annular valve housing is typically used. Attachment of the suture cuff to the valve may be through any of a number of different retention techniques, some of which provide rotatable coupling. For example, U.S. Pat. No. 5,360,014 shows a separate stiffening ring which carries a suture cuff and which is clipped to the valve body by a lock wire between the valve body and the stiffening ring.

There has been an ongoing effort to improve the efficiency of prosthetic heart valves. One critical factor in heart valve efficiency is the total area of the lumen when the leaflets are in an open position. For patients with small aortic roots (typically defined as a tissue annulus diameter of between about 17 mm and about 21 mm), there have been indications that available prosthetic valves are stenotic when compared to the healthy native valve. The orifice or lumen area of typical prosthetic valves is so small that the left ventricle may be unduly burdened in maintaining an adequate cardiac output. The effective orifice area is further reduced by the hydrodynamic impedance of the valve. It has been found that currently available small prosthetic aortic valves are associated with decreased tolerance to exercise, reduced rate of regression of left ventricular hypertrophy and a higher incidence rate of congestive heart failure. (See "Prosthetic Valves for the Small Aortic Root," *Journal of Cardiac Surgery*, 1994; 9[suppl]: 154–157, by H. B. Barner, A. J. Labovitz and A. C. Fiore.)

One technique which provides a less stenotic replacement valve involves enlargement of the aortic root and tissue annulus by the surgeon. However, such procedures introduce additional risk to the patient because they require greater manipulation and excision of tissue. Further, these procedures require an increased duration of heart-lung bypass, thereby imposing additional risks to the patient from that procedure. Another surgical approach for implanting a less stenotic valve has been to implant tissue valves such as allografts and stentless heterografts in these patients. However, for many patients, the well-established durability of mechanical heart valves is preferred.

To meet the need for less stenotic small prosthetic heart valves, changes in mechanical valve sewing cuff configurations have been introduced. This has allowed implantation of valves having a lumen diameter typically one size (2 mm) larger than has been previously possible. For example, the tissue annulus of the standard mechanical heart valve from St. Jude Medical, Inc., of St. Paul, Minn., lies on sewing cuff fabric which extends from a pyrolytic carbon orifice ring. In the Hemodynamic Plus (HP) Series mechanical heart valve also available from St. Jude Medical, Inc., the sewing cuff lies entirely between cuff retaining rims of the orifice ring so that the cuff is implanted supra-annularly and the upstream retaining rim periphery or circumference constitutes the valve surface (the "valve tissue annulus") engaging or apposing the heart's tissue annulus which remains after excision of the native valve. The intra-annular and subannular projection of this valve reduces the potential for tissue overgrowth of the valving mechanism and maintains the patency of the valve and tissue lumens.

Another prior art prosthetic heart valve is depicted in U.S. Pat. No. 5,360,041, issued Nov. 1, 1994. In this configuration, the valve is completely supra-annular. The suture cuff forms a brim which surrounds the extreme edge of the upstream annulus of the orifice ring. Although this may allow for increased valve and lumen size, the high supra-annular profile of the valve has, in at least some patients, blocked the right coronary ostium. Further, the position of the suture cuff may render the valving mechanism relatively vulnerable to tissue overgrowth. In addition, there is no intra-annular barrier to retard growth of tissue into the valve lumen.

While recent developments in prosthetic heart valves, such as those described above, have provided improvements, they remain stenotic compared to the healthy native valve. Improvements to further decrease the transvalvular pressure gradients of forward blood flow would be beneficial to patients. Although small, non-stenotic replacement valves are typically needed for the aortic position, there is also a need for such valves for the mitral position, typically in pediatric cases.

Another problem which may be associated with replacement heart valves with small lumens relates to formation of thrombus and thromboembolism. Thrombus and thromboembolism are known complications of mechanical heart valves and can result in serious disability or death. To help prevent these complications, a common treatment involves life-long anticoagulant therapy. However, anticoagulant therapy itself leads to an increased risk of anticoagulant-related hemorrhage.

Factors which influence the risk of thrombus and thromboembolism formation for mechanical heart valve patients include the nonphysiological surfaces and blood flow introduced by mechanical valves. Further, typical mechanical heart valves subject the blood to high shear stress, largely because the relatively small lumens of such valves tend to produce high velocity forward flow as the heart strives to maintain adequate cardiac output. Since the blood flow velocity immediately adjacent to the walls of the valve lumen and the occluders must be zero, large velocity gradients are generated during forward flow as a consequence of the high mean velocity. The shear stresses are proportional to the velocity gradients. High shear stresses are known to activate blood platelets and damage red blood cells. Such damaged red blood cells release a biochemical agent, adenosine 5'-diphosphate (ADP), which further activates platelets. The activated platelets have the potential to be deposited on the valve or downstream from the valve and to aggregate into thrombi. Furthermore, the activated platelets and the released biochemical agents initiate a coagulation cascade. Therefore, valves with mean forward flow velocities and peak shear stresses which are lower than prior art valves would be beneficial to patients.

SUMMARY OF THE INVENTION

A heart valve prosthesis for implantation in the heart of a patient includes a valve housing or body providing a lumen therethrough. At least one occluder in the lumen coupled to the valve body is movable between an open position allowing blood flow through the lumen and a closed position in which blood flow through the lumen is blocked. The valve housing includes a first annulus and a second annulus spaced apart from the first annulus. The first and second annuli are on opposite ends of the valve housing. A suture cuff is provided for attaching the valve housing to heart tissue of a patient.

A cuff retention mechanism is positioned between the first and second annuli for attaching the suture cuff to the valve housing. The suture cuff and at least the part of the cuff retention mechanism nearer the tissue annulus is spaced apart from the first annulus and the second annulus, providing tissue impingement barriers therebetween. The absence of suture cuff and cuff retention mechanism from the impingement barrier at the tissue annulus facilitates efficient lumenal utilization of the available tissue annulus area and thereby provides a significant beneficial feature.

In one embodiment, the cuff retention mechanism includes first and second rims which protrude from the valve housing. In another embodiment, the retention mechanism includes a single rim protruding from the valve housing. The cuff retention mechanism supplies support to the valve housing thereby strengthening the valve housing.

BRIEF DESCRIPTION OF THE DRAWINGS

FIG. 2A is a cross-sectional view showing a heart valve in accordance with the invention implanted in a heart.

FIG. 2B is a cross-sectional view of the heart valve of FIG. 2A rotated 90° attached to a heart.

FIG. 4 is a cross-sectional view of a heart valve in accordance with another embodiment attached to a heart.

FIGS. 13A, 13B, 14A and 14B are cross-sectional views of heart valve prostheses used to illustrate one aspect of the invention.

FIG. 16 is a cross-sectional view of a heart valve prosthesis having rims in accordance with another embodiment.

DETAILED DESCRIPTION OF THE PREFERRED EMBODIMENTS

Figure 1A:
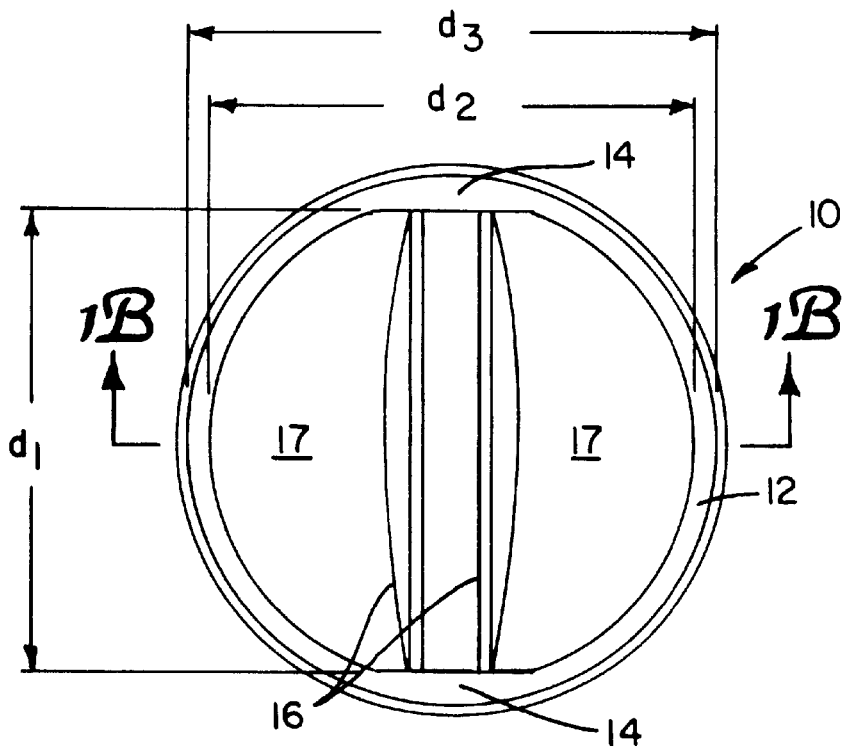
FIG. 1A is a top plan view of a heart valve without a suture cuff in accordance with the invention.

For implantation of a prosthetic valve in the aortic position, a surgeon typically opens the aorta and excises the native valve. The surgeon then inserts the prosthetic valve through the opening in the aortic wall and secures the prosthesis at the junction of the aorta and the left ventricle. The inflow annulus of the valve aces the left ventricle and, relative to the surgeon's perspective, may be termed the distal annulus, while the outflow annulus of the valve faces the aorta and may be termed the proximal annulus.

For implantation of a prosthetic valve in the mitral position, a surgeon typically opens the left atrium and excises the native valve. The surgeon then inserts the prosthetic valve through the opening in the atrial wall and secures the prosthesis at the junction of the left atrium and the left ventricle. The inflow annulus of the valve faces the left atrium and, relative to the surgeon's perspective, may be termed the proximal annulus, while the outflow annulus of the valve faces the left ventricle and may be termed the distal annulus. Thus, the distal portion of the valve may be defined as the portion of the valve typically seated intra-annularly, for either the aortic or mitral position.

The invention provides an improved heart valve prosthesis with an increased valve lumen achieved through a thin intra-annular barrier and placement of cuff and retention members supra-annularly to the tissue annulus. A cuff retention mechanism is provided between a first inflow annulus and a second outflow annulus of the orifice housing of the valve. In one embodiment, the cuff retention mechanism includes first and second rims which protrude from the valve orifice housing, with each rim spaced apart from its respective nearer annulus, thereby allowing the valve to be used for either aortic or mitral replacement while maintaining all the invention's beneficial features. In a second embodiment, the retention mechanism is a single rim protruding from the valve orifice housing and spaced apart from either annulus. In a third embodiment with two rims, only one rim is spaced apart from its nearer annulus while the other rim extends along its nearer annulus. This embodiment maintains all the beneficial features of the invention only when used either as an aortic replacement, for the case when the upstream rim is spaced from its annulus, or as a mitral replacement, for the case when the downstream rim is spaced from its annulus. In a fourth embodiment, the cuff retention mechanism includes a metal or polymer cuff retaining ring, the inner surface of which includes at least one radial projection, such as a key or rim, which mates with at least one circumferential groove or slot on the exterior of an orifice housing without rims, and spaced apart from the annuli, so as to prevent significant motion of the cuff retention mechanism parallel to the central or flow axis of the valve after assembly. In a fifth embodiment, the groove or slot lies in a thicker section of the orifice which is spaced apart from an annulus. In a sixth embodiment, a thin section or lip extends intra-annularly from a suture cuff retention ring which captures the valve housing. In at least one embodiment, the cuff retention mechanism provides support and stiffness to the valve housing, thereby helping assure that the occluders are not inadvertently released by surgical manipulations. In another embodiment, a rim may be interrupted or discontinuous or a groove may be formed between the rims.

Figure 1B:
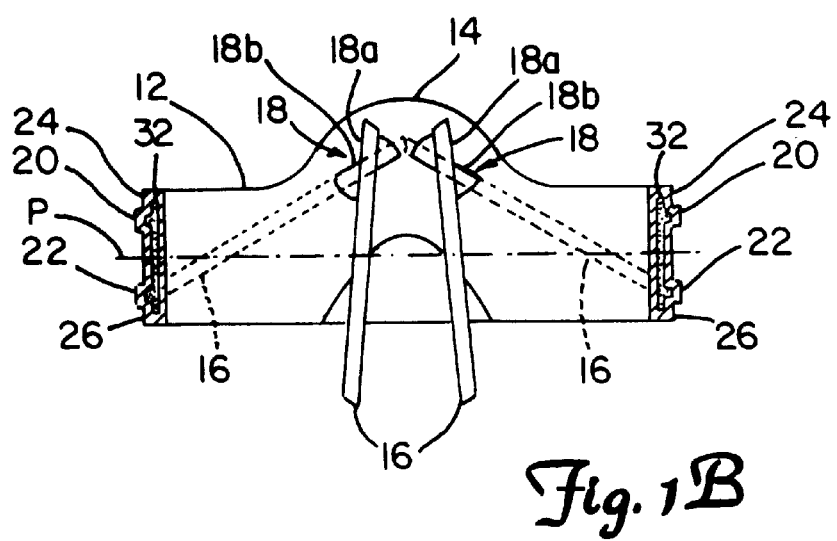
FIG. 1B is a cross-sectional view of the heart valve shown in FIG. 1A.
Figure 1C:
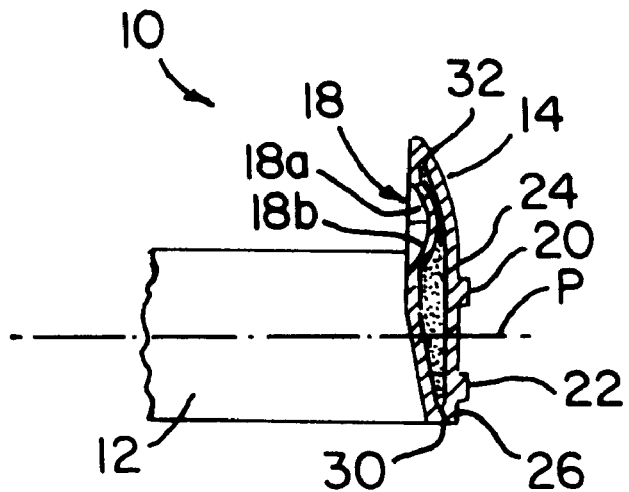
FIG. 1C is a cross-sectional view of the heart valve depicted in FIG. 1A.

FIGS. 1A, 1B and 1C are top plan and cross-sectional views, respectively, of heart valve 10 in accordance with the invention with the suture cuff not illustrated. Valve 10 includes a generally ring-shaped orifice support housing (also referred to as an orifice, orifice ring or orifice body) 12 forming a lumen 17 and having pivot guards 14. Pivot guards 14 include occluder mated spherical pivots 18 having opening stop 18a and closing stop 18b for occluders or leaflets 16. In FIG. 1A, leaflets 16 are shown in an open position while in FIG. 1B leaflets 16 are shown in the open position and in the closed position in phantom.

As shown in FIG. 1B, orifice body 12 includes generally circumferential body protrusions (or rims) 20 and 22. Protrusions 20 and 22 are spaced apart from either annulus of the orifice and toward a central plane P of orifice 12 to provide thin projections or lip portions 24 and 26. Lips 24 and 26 provide an engagement surface for the tissue annulus of a heart. For aortic and mitral replacement valves, respectively, the peripheries of lips 24 and 26 are tissue impingement barriers. Lips 26 and 24 serve as barriers to tissue encroachment into the valve lumen from the tissue which grows into the suture cuff. A sewing ring or suture cuff 50 (shown in FIGS. 2A and 2B) is attached between rims 20 and 22.

Generally, in preferred embodiments described herein, the orifice may consist of a pyrolytic carbon coating 30 which is deposited onto a graphite substrate 32 by a chemical vapor deposition (CVD) process.

Turning now to FIGS. 2A and 2B, aortic implantation of heart valve 10 in heart 40 is shown in cross section. FIG. 2B is similar to FIG. 2A except valve 10 is rotated 90°. Heart 40 includes aorta 42, left ventricle 44 and coronary ostium 46. Valve 10 is shown positioned in heart tissue annulus 48. Valve 10 includes an inflow annulus 27 and an outflow annulus 29. Lip 24 is adapted to receive tissue annulus 48 between rim 20 and the inflow annulus 27 of orifice 12 proximate the left ventricle 44. FIGS. 2A and 2B also show suture cuff 50 secured between rims 20 and 22. Suture cuff 50 is used to suture valve 10 to heart tissue, thereby securing valve 10 in position as shown in FIGS. 2A and 2B and preventing perivalvular leakage.

As shown in FIGS. 2A and 2B, lips 24 and 26 act as tissue impingement barriers to prevent ingrowth of heart tissue into orifice 12. Lip 24 provides an orifice annulus for engagement or apposition with the tissue annulus 48 of heart 40. The upstream 51 and downstream 53 planes of sewing cuff 50 are generally located within the confines of rims 20 and 22. Cuff 50 and rims 20 and 22 are entirely supra-annular in implanted valve 10. Lip 24 provides an extension of the orifice 12 into the plane of the tissue annulus 48. The outside diameter of orifice 12 at lip 24 generally conforms to the inside diameter of tissue annulus 48. Additionally, a portion of lip 24 is intra-annular with pivot guards 14 extending subannularly. The intra-annular projection of lip 24 reduces the probability of overgrowth of tissue from tissue annulus 48 into the valve lumen. This is advantageous since such tissue overgrowth tends to reduce the lumen area, disturbs the flow and may encroach on the valve mechanism, reducing the effectiveness of the heart valve. The subannular extension of pivot guards 14 reduces the height of orifice 12 protruding into the aortic root thereby reducing the likelihood of blockage of coronary ostium 46. Lip 26 may be used to reduce tissue growth progressing from the cuff 50 onto the outflow annulus 29 and into the valve lumen 17.

For the mitral position, lip 26 is positioned intra-annularly, and lip 24 and pivot guard 14 are positioned supra-annularly. Lip 24 may be used to reduce the probability of tissue growth progressing from cuff 50 onto the inflow annulus 27 and into the valve lumen 17.

Figure 3:
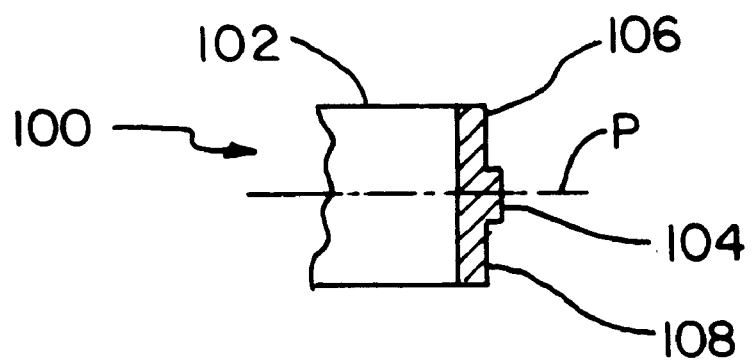
FIG. 3 is a cross-sectional cutaway view of a portion of a heart valve in accordance with another embodiment of the invention.

FIG. 3 shows a cross-sectional view of a portion of a valve 100 in accordance with a second embodiment. Valve 100 includes orifice housing 102, including single protrusion rim 104. Single rim 104 is positioned proximate plane P through the approximate center of orifice 102. Tissue impingement barrier lips 106 and 108 are formed on either side of rim 104 between rim 104 and the ends of orifice 102. A suture cuff 110 (shown in FIG. 4) is attached to rim 104.

FIG. 4 is a cross-sectional view of valve 100 implanted in heart 40. Numbering of similar elements in valve 100 is consistent with those elements in valve 10. In FIG. 4, valve 100 includes suture cuff 110 which is used by a surgeon to suture valve 100 to tissue of heart 40. As shown in FIG. 4, the seating and engagement of valve 100 in tissue annulus 48 is similar to that of valve 10 shown in FIGS. 2A and 2B. Cuff 110 and the majority of orifice 102 is supra-annular. For aortic implantation, tissue impingement barrier lip 106 is intra-annular while pivot guards 14 extend subannular.

Figure 5:
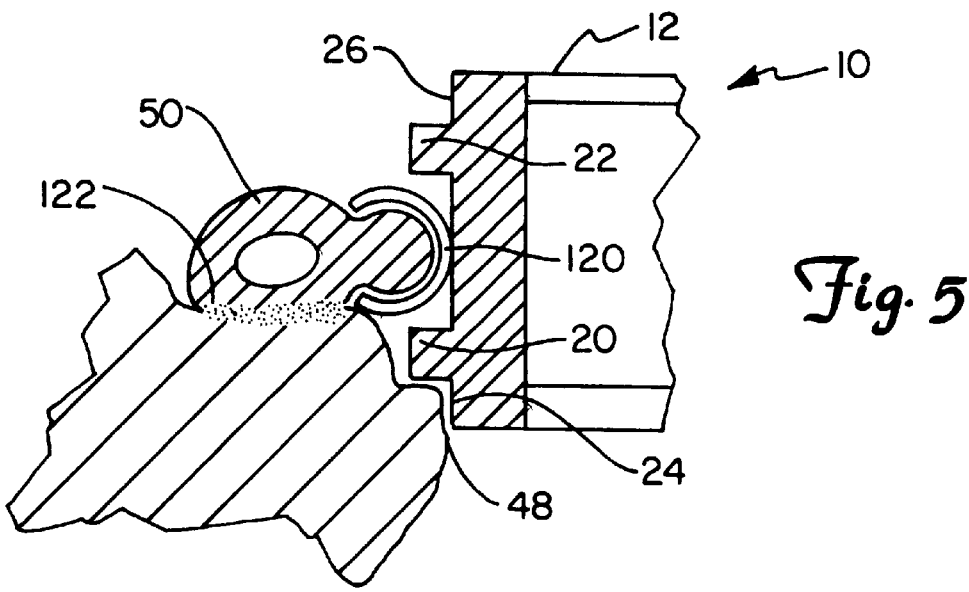
FIG. 5 is a cross-sectional view showing a suture cuff attached to the heart valve depicted in FIG. 1A.

FIG. 5 is a cross-sectional view of valve 10, as shown in FIGS. 1A, 1B, 1C, 2A and 2B, which shows attachment of suture cuff 50 to orifice 12. A metal, polymer or other biocompatible material attachment ring 120 fits between rims 20 and 22 and pinches or clamps cuff 50. Cuff 50 comprises, for example, a polyester or PTFE knit or a PTFE felt, or other soft, conformable material known in the art.

FIG. 5 shows the initiation of tissue ingrowth 122 into cuff 50 from the heart tissue adjacent tissue annulus 48. Assembly of the suture cuff to the orifice may be through any appropriate technique known in the art. In one embodiment, ring 120 is initially in a flattened condition such that the tips of the "U" shape are spread apart. Ring 120 is placed between rims 20 and 22 using a relatively uniform expansion technique in which ring 120 is slid over a conical mandril (not shown) and over one of the two rims 20,22 until it is positioned as shown in FIG. 5. Ring 120 is a stiffener for the orifice and can be used to attach the cuff in a rotatable manner Cuff 50 is placed around the outer circumference of ring 120 and the sides of ring 120 are bent as shown in FIG. 5. Friction between cuff 50 and ring 120 maintains cuff 50 in position. Additionally, sutures, staples, pins, adhesives or other such device or material may be used to adhere cuff 50 to ring 120 or directly to orifice 12.

Figure 6:
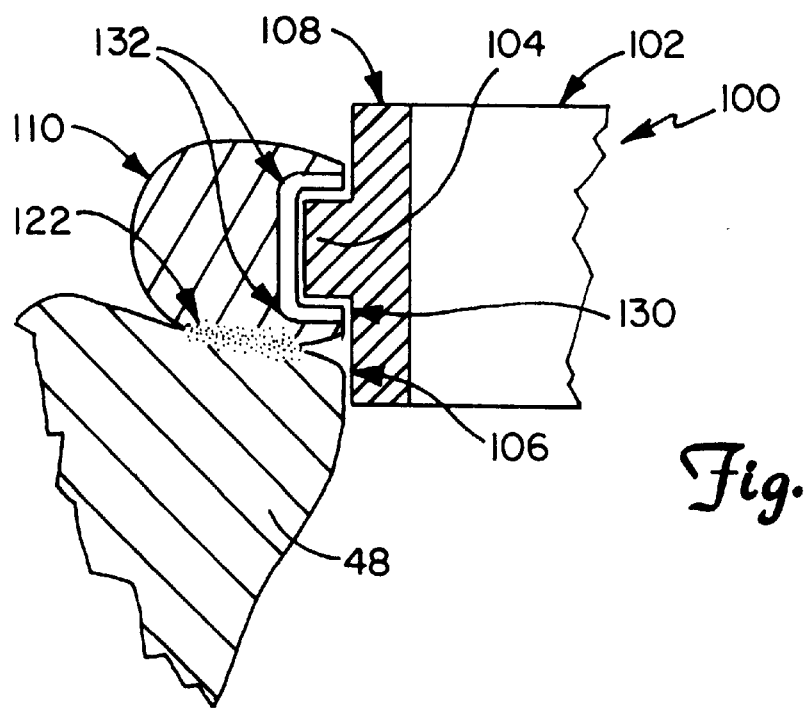
FIG. 6 is a cross-sectional view showing a suture cuff attached to the heart valve depicted in FIG. 4.

FIG. 6 is a cross-sectional view of a portion of valve 100 shown in FIGS. 3 and 4, providing a detailed view showing attachment of suture cuff 110 to orifice 102 at rim 104. A metal, polymer or other biocompatible material attachment ring 130 is attached to cuff 110 and crimped around and onto rim 104. Prior to attachment, ring 130 lies relatively flat. Scoring 132 is provided on ring 130 to promote bending of ring 130 at the desired locations. Ring 130 is crimped by applying pressure to opposing sides of ring 130 such that ring 130 bends at scoring points 132.

Figure 7:
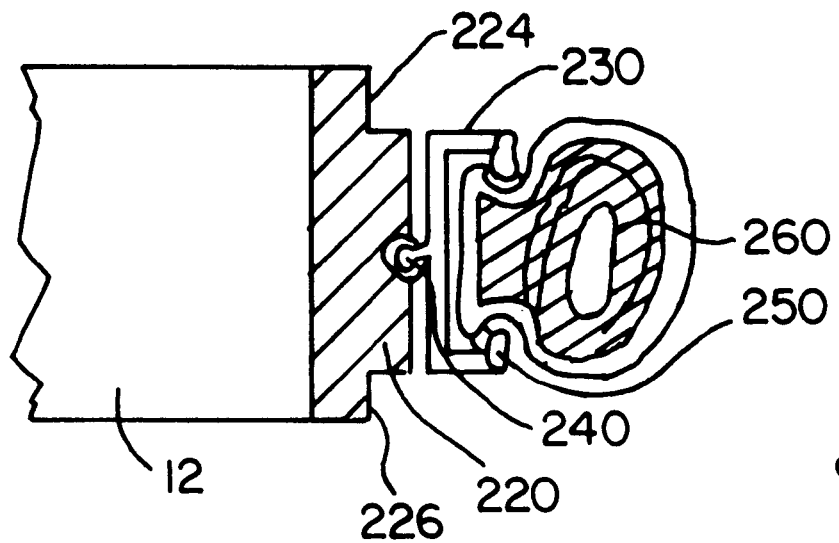
FIG. 7 is a cross-sectional view showing a suture cuff attached to a heart valve in accordance with another embodiment.

FIG. 7 is a cross-sectional view showing orifice 12 having rim 220 forming tissue impingement barriers 224 and 226. Rim 220 includes groove 230 formed therein. A mating key or rim 240 of cuff retaining ring 250 engages mating groove 230 of orifice 12. Rim 220 of orifice 12 is of sufficient thickness to form groove 230 therein without deleteriously decreasing the strength of orifice 12. Cuff 260 is captured in ring 250.

Figure 8:
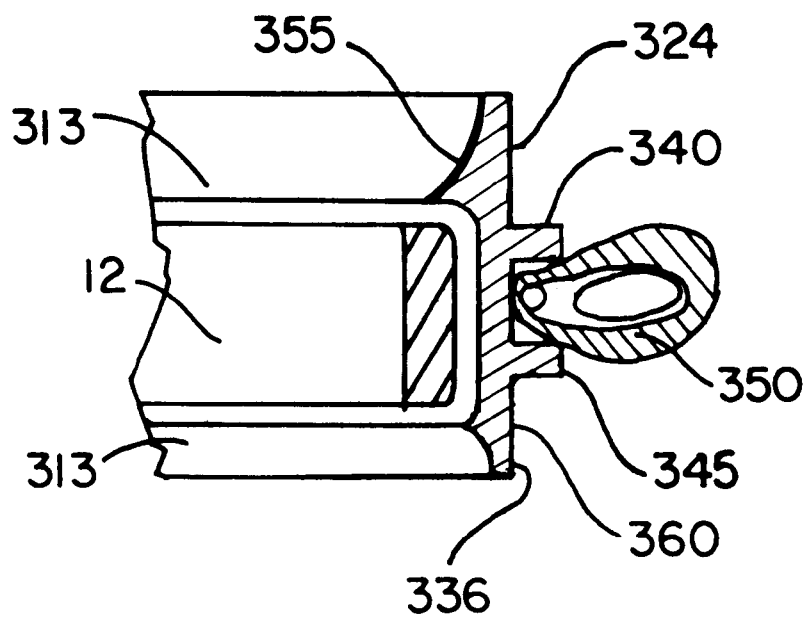
FIG. 8 is a cross-sectional view showing a suture cuff attached to a heart valve in accordance with another embodiment.

FIG. 8 is a cross-sectional view of orifice 12 having a cuff retention mechanism in accordance with another embodiment in which a projection from the cuff retention mechanism ring itself forms a tissue impingement barrier and inflow or outflow annuli. Cuff 350 is retained between rims 340 and 345 of ring 360. Tissue impingement barriers 324 and 326 are formed between extensions of ring 360. Ring 360 comprises a biocompatible metal such as titanium or cobalt-chrome alloy and extends past the valve housing so as to serve as the tissue impingement barrier. Cuff 350 may be retained by suture 355 wrapped around the annulus formed between rims 340 and 345. Radially inward extensions 313 capture orifice 12.

Figure 9:
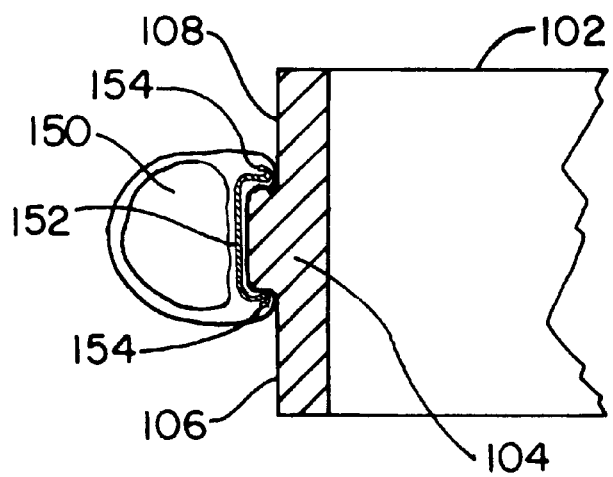
FIG. 9 is a cross-sectional view showing a suture cuff attached to a heart valve in accordance with another embodiment.

FIG. 9 is a cross-sectional view of orifice 102 attached to cuff 150 in accordance with another embodiment. A spring clip ring 152 extends around the outer circumference of orifice 102 and grasps rim 104. Preferably, cuff 150 is formed around spring clip ring 152. The cuff clip assembly is snapped onto valve rim 104. Alternatively, ring 152 includes tips 154 which clamp the fabric of suture cuff 150.

Figure 10:
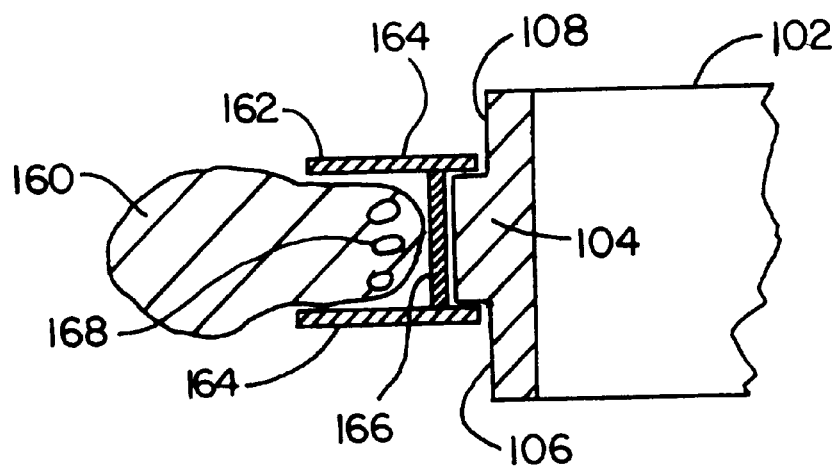
FIG. 10 is a cross-sectional view showing a suture cuff attached to a heart valve in accordance with another embodiment.

FIG. 10 is a cross-sectional view of orifice 102 attached to suture cuff 160 in accordance with another embodiment. Attachment mechanism 162 includes disks 164 which extend around the outer circumference of orifice 102. Disks 164 are connected together by band 166 which provides a friction fit with rim 104 of orifice 102. Sewing cuff 160 is secured to band 166 between disks 164 by suture windings 168. In alternative embodiments, disks 164 and band 166 can be formed integrally as a single piece or separately and attached together. This may be through the use of a biocompatible adhesive, or similar material, or a friction fit between protrusions from band 166 and openings in disks 164.

In prior art, the stiffness of the orifice has typically been increased by increasing the area of the orifice wall section, which for a given tissue annulus diameter reduces the area of the lumen. One aspect of this invention includes providing the orifice stiffness for a given tissue annulus diameter without reducing lumen area. In one or more embodiments of the current invention the stiffness of the orifice is enhanced by rims projecting from the orifice. It has been discovered and demonstrated that the size, shape and placement of the rims enhance the stiffness.

Figure 11:
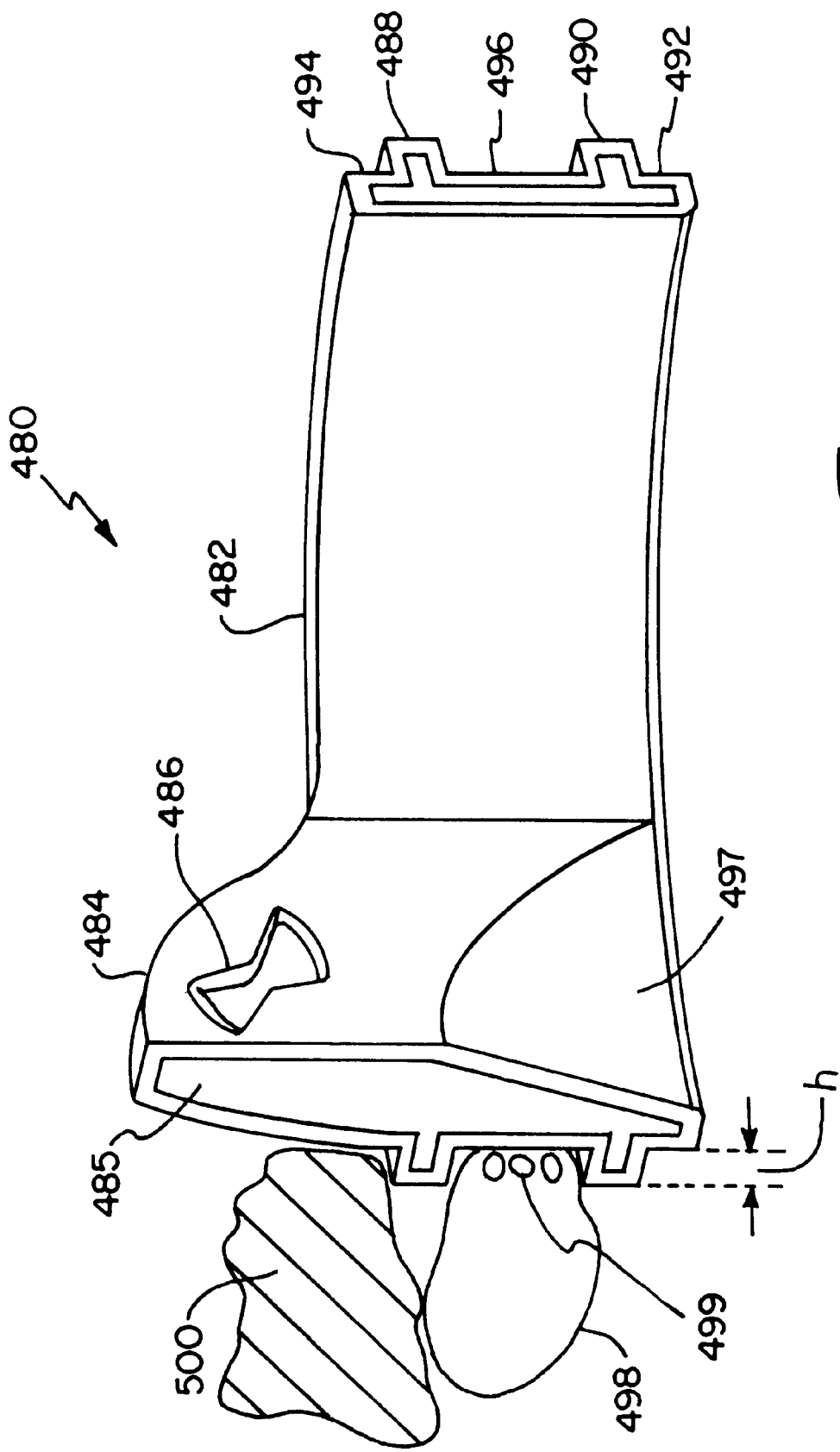
FIG. 11 is a cross-sectional view of a heart valve prosthesis in accordance with another embodiment.

FIG. 11 shows a cross-sectional view of a heart valve prosthesis orifice 480 in the aortic position in accordance with another embodiment which includes housing 482 and pivot guard 484 which carries a pivot 486. Housing 482 is formed on substrate 485. Rims 488 and 490 extend around the outer circumference of housing 482 and form outflow proximal implant lip 492 and inflow distal lip 494. A middle surface 496 is formed between rims 488 and 490. A suture cuff 498 fits between rims 488 and 490 around middle surface 496 and is used to attach heart valve orifice 480 to heart tissue annulus 500. The size of orifice 480 is selected such that tissue annulus 500 substantially conforms to the diameter of distal lip 494. However, the majority of orifice 480 and suture cuff 498 are positioned supra-annular relative to tissue annulus 500.

Rims 488 and 490 have a radial height h which is greater than that of typical prior art designs. In a preferred embodiment, h is greater than about 0.25 mm and is preferably about 1 mm. It has been discovered that by increasing the dimension h, additional stiffness is provided to housing 482. Additionally, the increase in the h dimension of rims 488 and 490 protects the cuff retention mechanism 499 of suture cuff 498. In one embodiment, retention mechanism 499 comprises sutures. However, any mechanism may be used such as a polymer or metal band or a ring. In one or more embodiments, retention mechanism 499 allows rotation of valve housing 482 relative to cuff 498 during the implantation procedure. The additional protection provided by rims 488 and 490 to the retention mechanism 499 helps reduce application of excessive pressures to mechanism 499 such as pressure from tissue annulus 500. Such excessive pressures tend to change the amount of torque required to rotate housing 482 relative to cuff 498. Furthermore, the increased height h of rims 488, 490 further reduce the likelihood of tissue ingrowth from tissue annulus 500 into the lumen 497 of orifice 480. Further still, the increased height h of rims 488,490 increases the ability to retain the suture cuff 498 between rims 488, 490.

Figure 12:
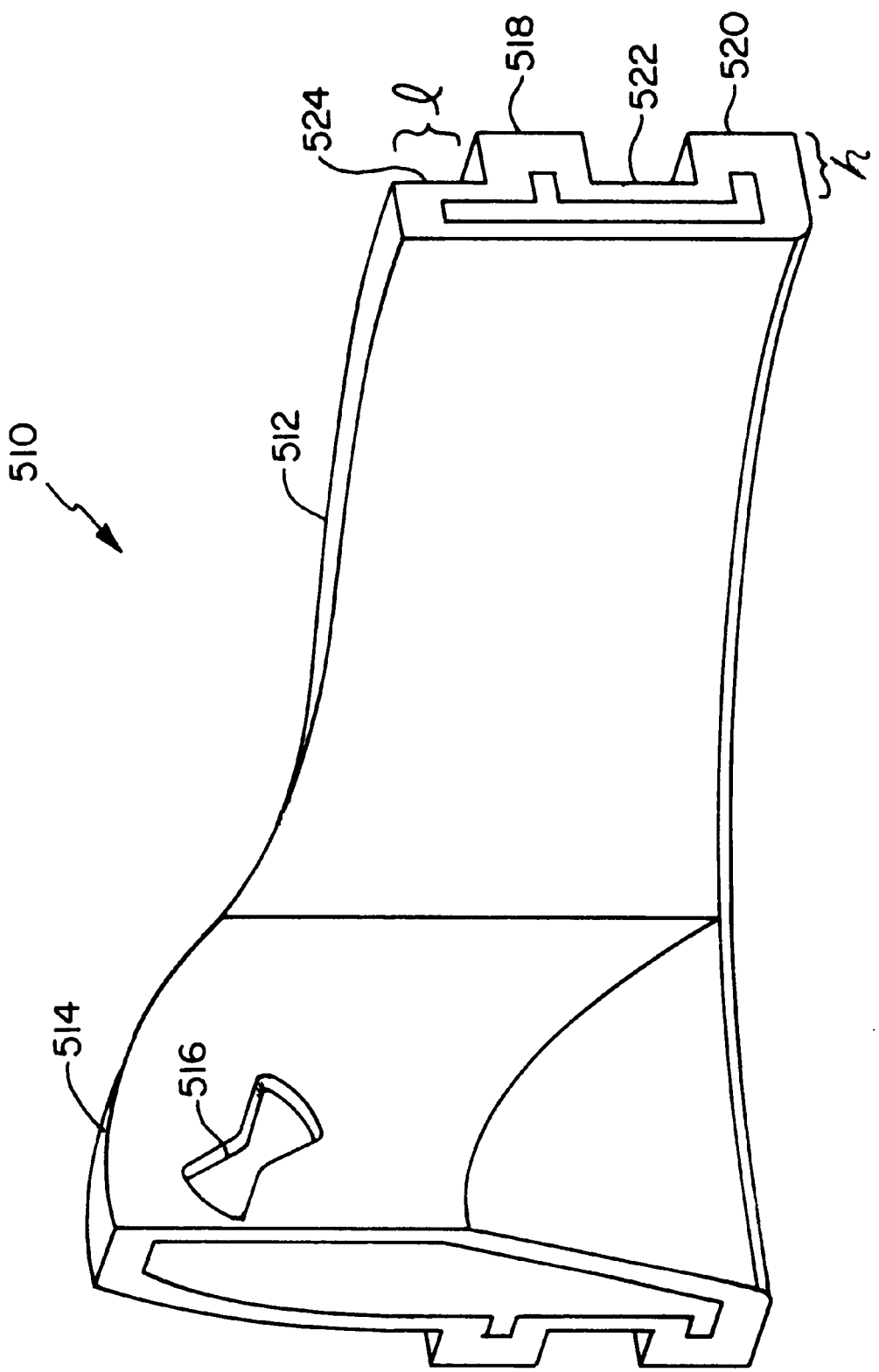
FIG. 12 is a cross-sectional view of a heart valve prosthesis in accordance with another embodiment.
Figure 13A:
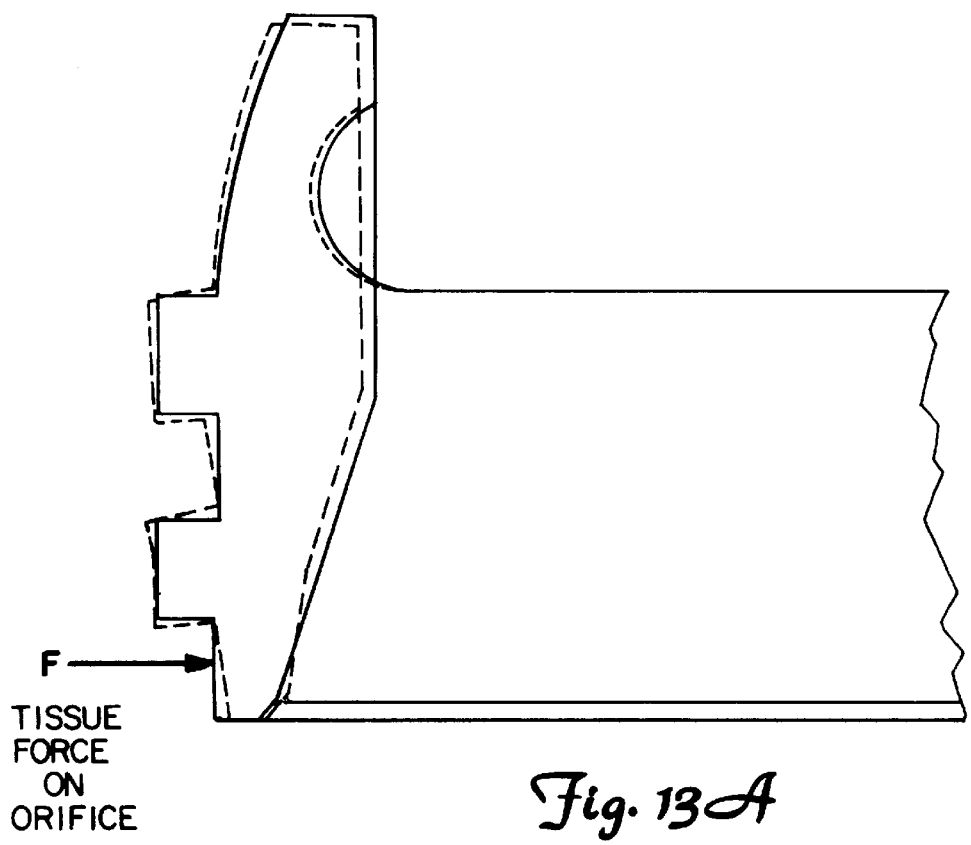
Figure 13B:
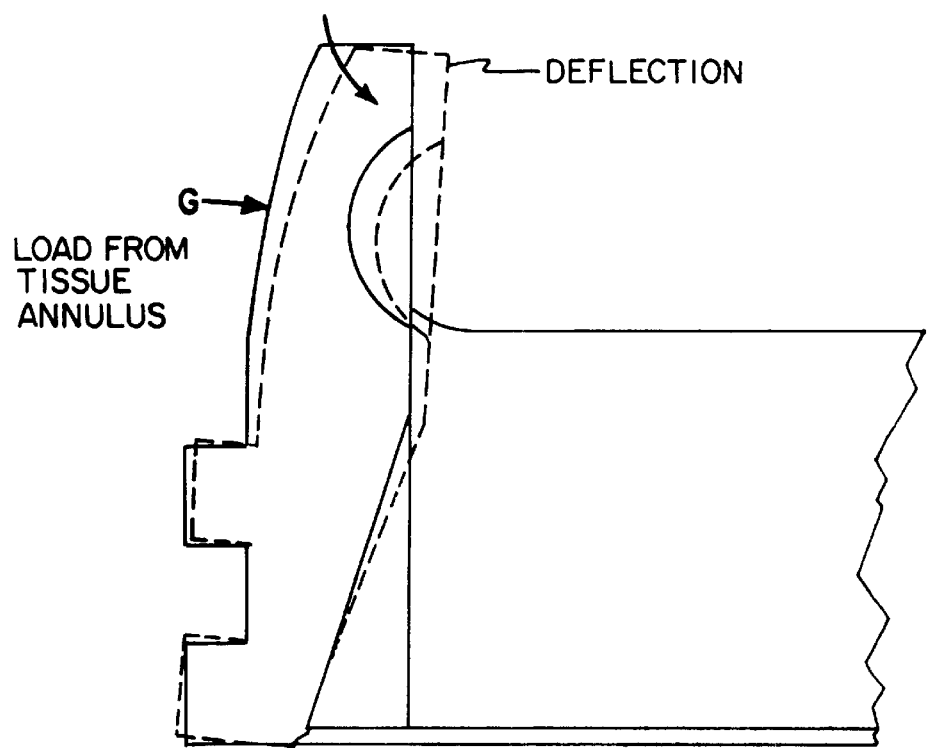

FIG. 12 is a cross-sectional view of another embodiment of heart valve prosthesis orifice 510 adapted for aortic implantation having housing 512. Housing 512 includes pivot guard 514 and pivot 516 formed therein. Distal rim 518 and proximal rim 520 extend around the outer circumference of housing 512 and form middle section 522 therebetween. Rims 518 and 520 are positioned toward the proximal side of prosthesis 510 and rim 518 forms distal lip 524 around the outer circumference of housing 512. It has been discovered that the offset configuration of rims 518 and 520 relative to housing 512 provides additional stiffness for a given lumen. This allows the interior lumen of housing 512 to be increased for a given stiffness. Therefore, the lumen area is increased while providing orifice stiffness. Furthermore, the configuration shown in FIG. 12 allows for greater length l of distal lip 524 which provides for deeper sub-annular placement and a larger intra-annular impingement barrier. It also decreases the valve supra-annular profile to reduce the potential for blockage of the coronary ostia. The design shown in FIG. 12 also includes an increased rim height h as described above for the embodiment of Figure FIGS. 13A and 13B show orifices 610 and 510, respectively. Orifice 610 is an embodiment adapted for implant in the mitral position, with pivot guards 620 supra-annular (in the left atrium) and orifice 510 is an embodiment adapted for implant in the aortic position, with pivot guards 520 sub-annular (in the left ventricular outflow tract). Orifice 610 is shown acted upon by hypothetical force F generated by the mitral valve tissue annulus. Orifice 510 is shown acted upon by hypothetical force G generated by tissues within the left ventricular outflow tract below the aortic annulus. FIGS. 14A and 14B are cross-sectional views of heart valve prostheses 480 and 510, respectively. FIGS. 13A, 13B, 14A and 14B are provided to illustrate the relationship between the placement of the rims and the stiffness of the prosthesis orifice. A comparison of the stiffness of valves 510 and 480 follows.

The stiffness, or ability of the housing to resist loading, is dependent on the orifice geometry and material elastic modulus. The present invention provides a technique for increasing stiffness for a given material. The method increases resistance to both translational and torsional loads on the orifice and to combinations thereof. The geometric parameter that is used to analyze and determine stiffness is the area moment of inertia which, for a given material, is directly proportional to stiffness. There are three area moments of inertia associated with an area, Ix, Iy and Jo (polar moment of inertia). The I moments are each associated with an axis in the plane of the area, such as x and y in FIGS. 14A and 14B, and the polar moment of inertia Jo is associated with rotation, and therefore, an axis perpendicular to the plane.

The polar moment of inertia of the area is the simple algebraic sum:

$$Jo = Ix + Iy \qquad \text{Eq. 1}$$

Thus, if either Ix or Iy is increased, the ability of the structure to resist rotation is increased.

Other important rules of area moments of inertia are:

The Additive Rule

For the orifice body, $Ix = Ix_1 + Ix_2 + Ix_3$ where $Ix_i$ is the moment of inertia of area i (where i=1,2,3) with respect to the x axis of the entire system.

The Parallel Axis Theorem $I_{xi} = I_{xilocal} + A_i D_i^2$ where $I_{xilocal}$ is the moment of inertia of area i with respect to its centroid and $A_i D_i^2$ is the transformation for the offset in the area's axis with respect to the system's axis. Quantity $D_i$ is the distance from the local area's x axis and the system's x axis and $A_i$ is the area of the local element. Furthermore, for a rectangle $I_{local} = (\text{Width} \times \text{Height}^3)/12$. Height and Width are relative to the axis of the moment, i.e., the width for Iy is the height for Ix. Equations of the same form are also true for Iy.

The difference between the orifice 480 and 510 is the distance "v" shown in FIGS. 14A and 14B, respectively. For the purpose of this explanation, all lettered dimensions are the same in orifice 480, 510, and orifices 480, 510 are made from the same material. This implies that the local I moments are equal for both designs since the heights and widths of the areas do not change. The only portion of the I moments that change is the parallel axis portion $AD^2$, specifically the D. It can be seen that the Dy of the system remains unchanged as dimension v is changed. Therefore, the Iy's are equal for both designs. The parallel axis portions ($D_i^2$) of Ix changes as area $A_3$ is shifted downward. One aspect of the invention for one or more embodiments moves structure away from the neutral axis. The change is described mathematically as follows:

Parallel Axis Theorem Portion

For the embodiment of FIG. 14A, valve 480, a prime sign ' will be used. Due to symmetry about the x axis, $D'_1 = 0$, $D'_2 = (z+H_2)/2$, and $D'_3 = -(z+H_2)/2$ For valve 480 shown in FIG. 14A $$Ix' = \Sigma I'_{xilocal} + A_1 D'^2_1 + A_2 D'^2_2 + A_3 D'^2_3 = \Sigma I'_{xilocal} + A_2((z+H_2)/2)^2 + A_3(-(z+H_2)/2)^2 \qquad \text{Eq. 2}$$

For Ix of valve 510 shown in FIG. 14B:

The neutral axis of the valve 510 is shifted downward and is assumed to be at the midpoint between the rims. The difference in stiffness is defined below.

For any given material the difference in stiffness is proportional to the differences in area moments of inertia.

Area stiffness is proportional to $I_x - I_x'$. Therefore, if $I_x > I_x'$, then the design is stiffer.

Given:

$$I'_{xilocal} = I_{xilocal} \qquad \text{Eq. 3}$$

Therefore:

$$I_x - I'_x = A_1 D_1^2 + A_2 D_2^2 + A_3 D_3^2 - [A_1 D'^2_1 + A_2 D'^2_2 + A_3 D'^2_3] \qquad \text{Eq. 4}$$

Since area $A_3$ is shifted downward the centroid will also be shifted downward thus causing $D_1 \neq 0$. Therefore;

$$A_1 D_1^2 > A D'^2_1 = 0 \qquad \text{Eq. 5}$$

$$D_2'^2 = D_3'^2 = \left(\frac{z + H_3}{2}\right)^2 \qquad \text{Eq. 6}$$

$$D_2^2 \approx D_3^2 \approx \left(\frac{z + v + H_3}{2}\right)^2 \qquad \text{Eq. 7}$$

Therefore:

$$A_2 D_2^2 > A_2 D_2'^2 \text{ and } A_3 D_3^2 > A_3 D_3'^2 \qquad \text{Eq. 8}$$

From this it can be seen that:

$$I_x - I'_x = [A_1 D_1^2 - A_1 D'^2_1] + [A_2 D_2^2 - A_2 D'^2_2] + [A_3 D_3^2 - A_3 D'^2_3] > 0 \qquad \text{Eq. 9}$$

The difference is positive therefore the area moment of inertia and stiffness are greater for the aortic or mitral specific design. The analytic derivation of the centroids and offsets have not been shown. However, one skilled in the art could derive these equations.

Figure 15A:
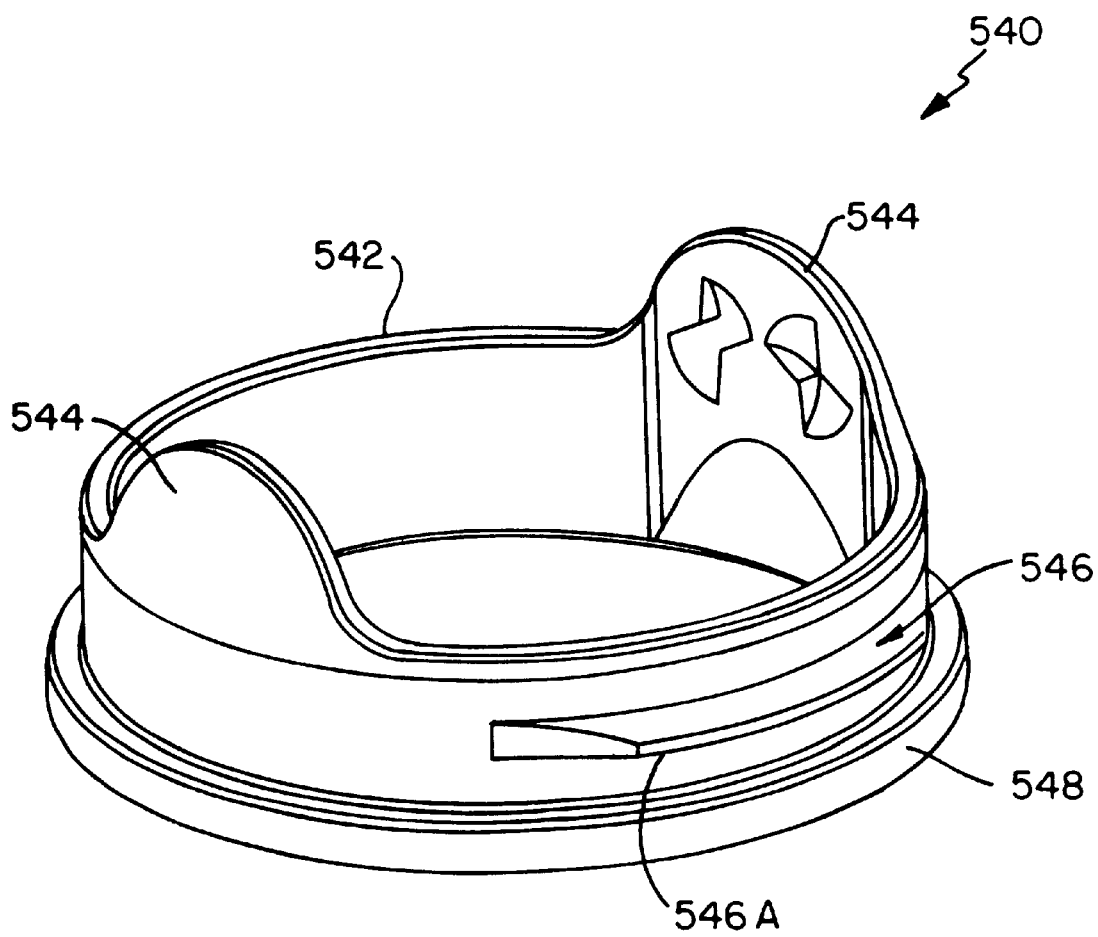
FIGS. 15A, 15B and 15C are perspective and side plan views of heart valve prostheses in accordance with another embodiment.
Figure 15B:
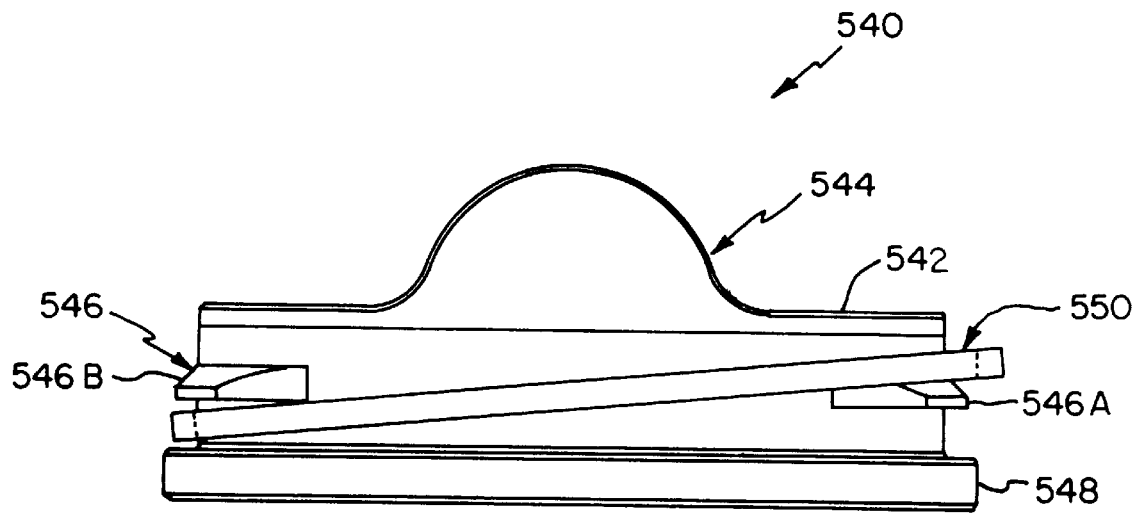
Figure 15C:
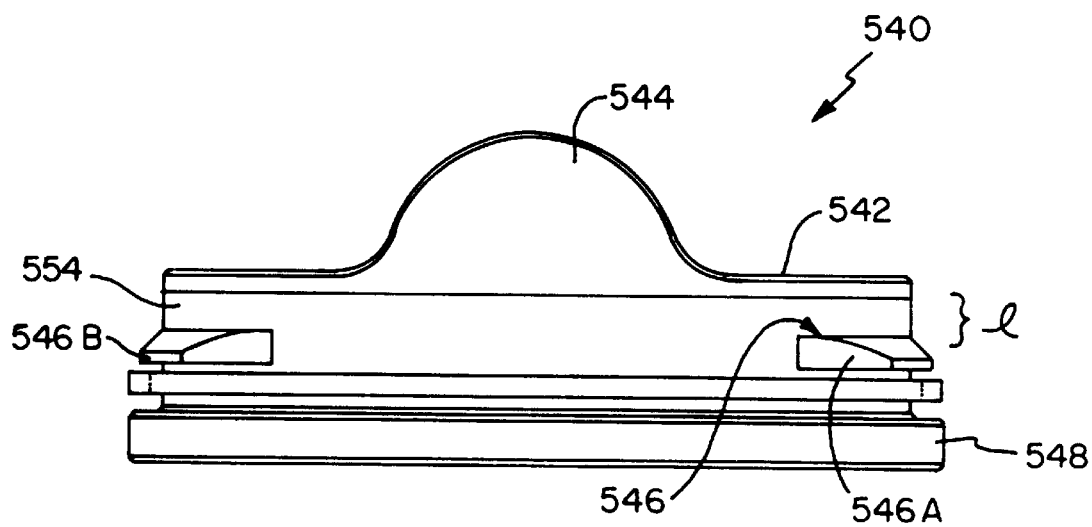

FIG. 15A is a perspective view and FIGS. 15B and 15C are side plan views of a heart valve orifice 540 in an aortic position in accordance with another embodiment. Orifice 540 includes housing 542, pivot guards 544, distal rim 546 and proximal rim 548. Proximal rim 548 is positioned similar to proximal rim 520 shown in the embodiment of orifice 510. However, distal rim 546 has two segments, 546A and 546B. FIGS. 15B and 15C show a retention ring 550 which may be used to attach, for example, a suture cuff to orifice 540. It has been discovered that it is desirable in some instances for ring 550 to be a continuous member. However, if ring 550 is continuous it must be stretched over a rim of a typical prior art prosthesis. Such a stretchable ring may perform poorly in retaining the cuff to the orifice. In contrast, ring 550 is a continuous stiff ring and is placed over rim 546 by placing ring 550 at an angle to the axis of prosthesis 540 as shown in FIG. 15B. As shown in FIG. 15B, first one side of ring 550 is slipped over segment 546B of rim 546 and then the other side of ring 550 is slipped over segment 546A as shown in FIG. 15B.

In the embodiment of prosthesis 540, proximal rim 548 is offset similar to FIG. 12 to provide the increased stiffness as discussed above. Furthermore, segments 546A and 546B are positioned between pivot guards 544 to increase the stiffness in the relatively compliant portion of housing 542. Specifically, pivot guards 544 provide stiffness to housing 542 and segments 546A and 546B are positioned between pivot guards 544 to provide additional stiffness in this region of housing 542. Furthermore, the proximal rim 548 of orifice 540 can resist the load of the aortic blood pressure applied to the closed valve. Proximal rim 548 provides additional stiffness to the proximal side of orifice 540 to accommodate these loads during implantation. Distal lip 554 has an enlarged length l (see FIG. 15C) to provide a better interface with the heart tissue annulus, similar to that discussed with respect to FIG. 12.

FIG. 16 is a cross-sectional view of a heart valve prosthesis 560 in an aortic position in accordance with another embodiment which includes housing 562 and pivot guard 564. Proximal rim 566 and distal rim 568 extend around the circumference of housing 562 and form a V-shaped groove 570 therebetween. Rims 566 and 568 are offset in a proximal direction with respect to the surgeon in a typical surgical approach to provide distal lip 572. Rims 566 and 568 extend over a relatively large area of the outer circumference of housing 562 and provide a slope to groove 570 which carries retention mechanism 574. This is in contrast with a typical rim in which there is a step thickness differential such as in FIG. 1B. Retention mechanism 574 may be any appropriate element to couple a suture cuff to groove 570 such as a V-shaped compliant or expandable ring, such as a spring ring.

Figure 17A:
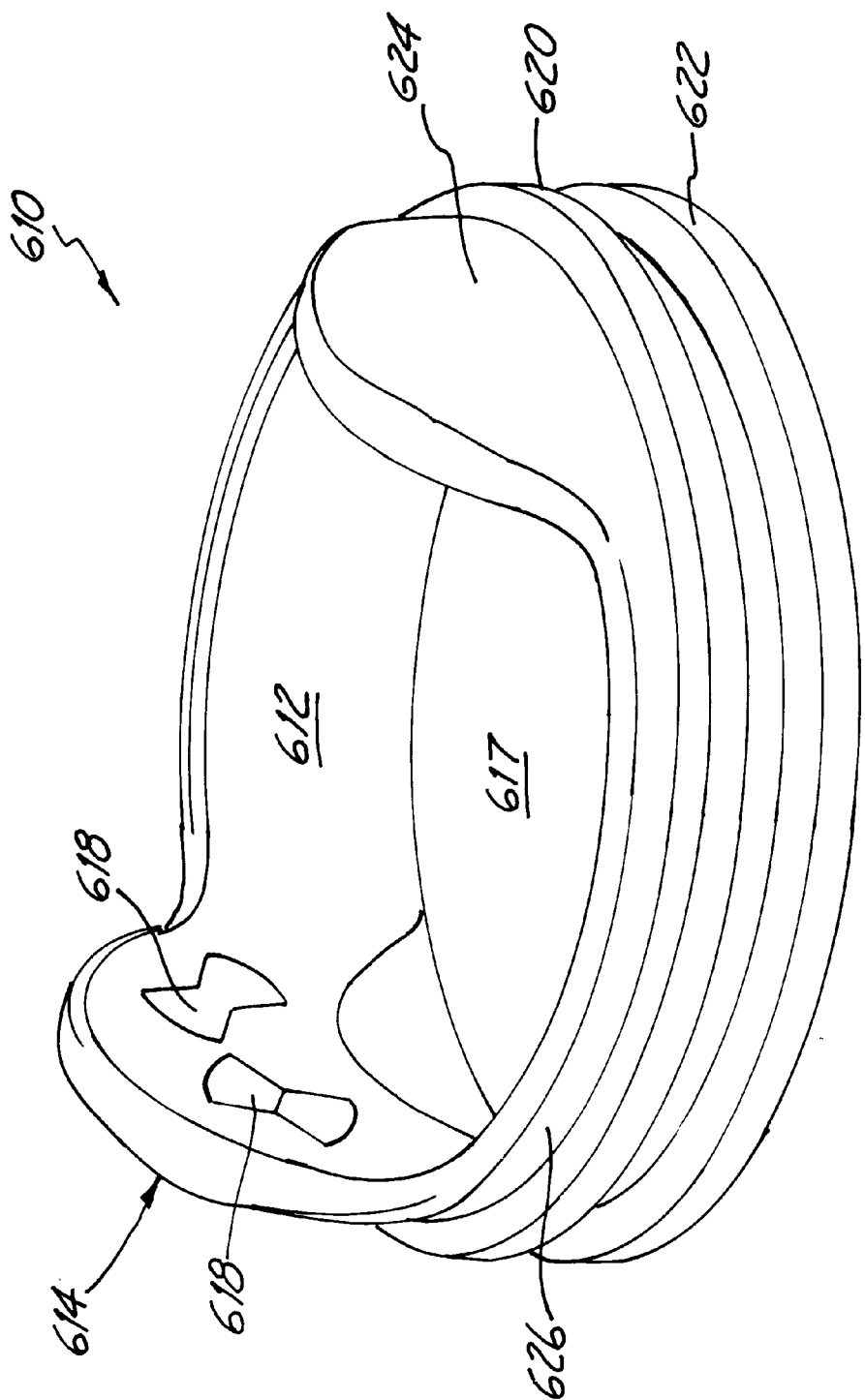
FIGS. 17A, 17B and 17C are side perspective, side perspective cutaway and side cross-sectional views, respectively of a heart valve prosthesis in accordance with another embodiment.
Figure 17B:
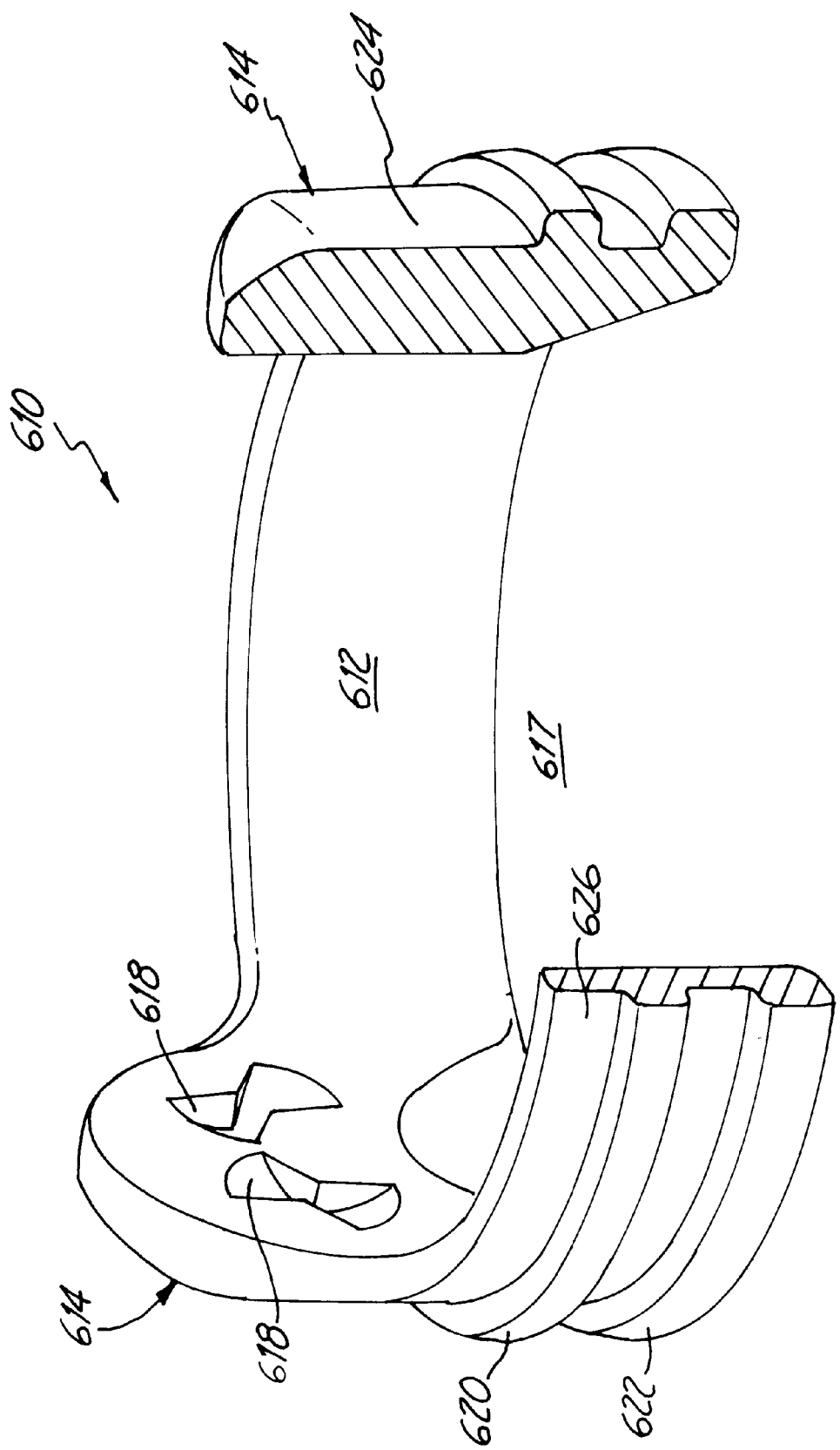
Figure 17C:
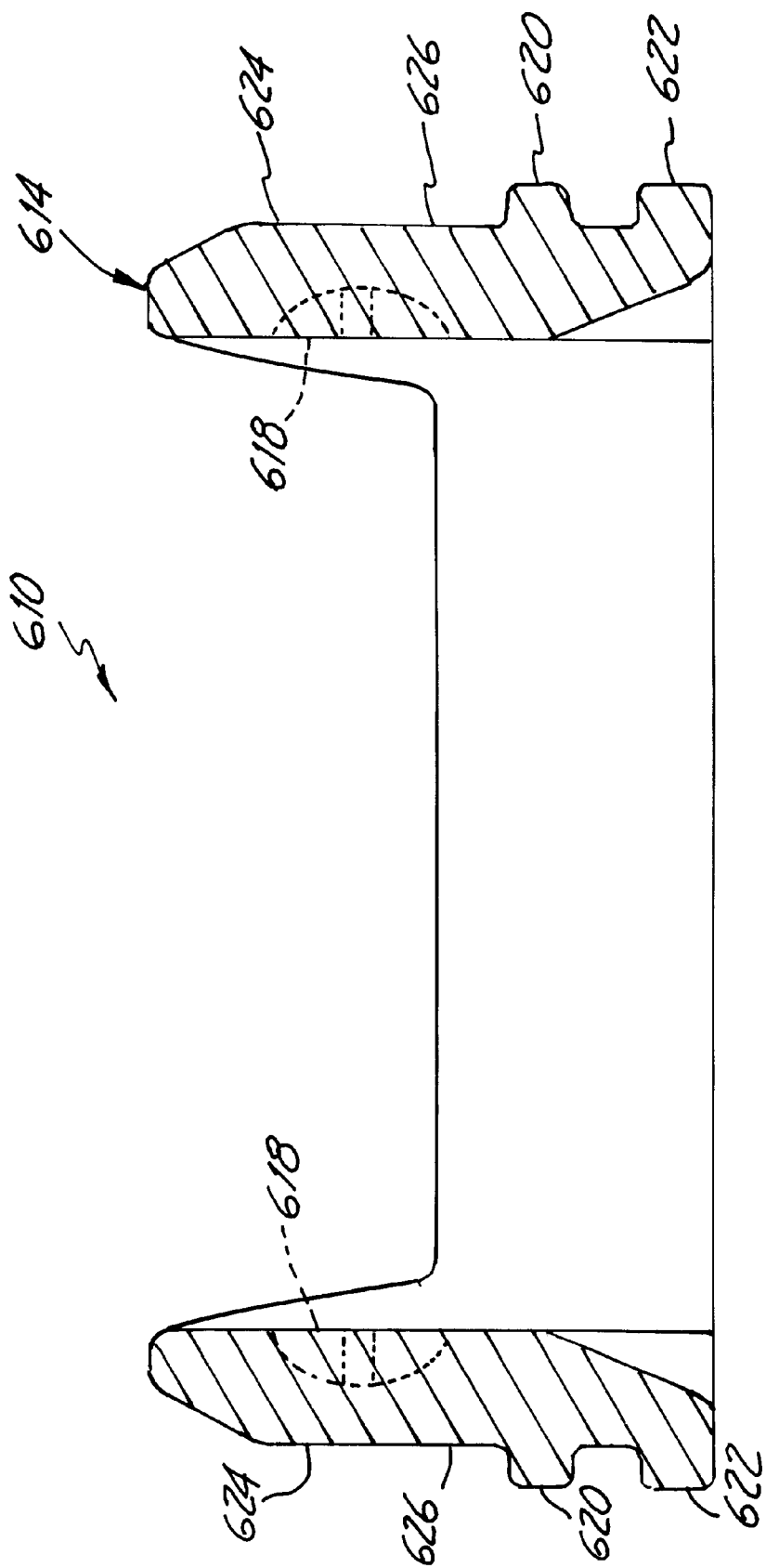

FIGS. 17A, 17B and 17C are side perspective, side perspective cutaway, and side cross-sectional views, respectively, of heart valve 610 in accordance with another aspect of the invention. Valve 610 includes a generally ring-shaped orifice support housing (also referred to as an orifice, orifice ring or orifice body) 612 forming lumen 617 and having pivot guards 614. Pivot guards 614 include occluder mated spherical pivots 618 for occluders or leaflets (not shown). Orifice body 612 includes generally circumferential body protrusions (or rims) 620 and 622. In the embodiment of FIGS. 17A–C, outer surfaces 624 of pivot guards 614 are substantially cylindrical and congruous with lip 626. Preferably, the outside diameter of pivot guard 614 is identical to the tissue annulus diameter. This is well adapted for fitting into the tissue annulus for aortic implantation. The design allows for an increased inner lumen for an identical size pivot. Further, the cylindrical shape provides additional material in comparison to a pivot guard having a prior art spherical shape. This additional material provides increased strength and stiffness to the pivot guard. The shape is also less expensive and easier to manufacture than a spherical pivot guard. The pivot guard is preferably positioned against the natural tissue annulus thus enhancing fluid flow characteristics of the valve. For example, any gap between the pivot guard and the tissue annulus is eliminated thereby reducing the zone, area of stagnation in the blood flow.

One aspect of the invention provides an increase in the effective orifice area of the orifice relative to the available tissue annulus 48 area of heart 40. As discussed above, a small prosthetic valve lumen in the aortic position results in high systolic transvalvular pressure gradients which excessively burden the left ventricle. Furthermore, a small lumen has been related to thrombus and thromboembolism formation. Factors relating to increased risk of thrombus and thromboembolism include the non-physiological surfaces and blood flows introduced by mechanical valves. Additionally, a small lumen results in increased shear stress due to higher mean velocity in the blood flow. An increase in lumen area as set forth herein provides reduced transvalvular pressure gradients and reduced mean velocity and thereby reduced shear stress, and therefore a reduction in the potential formation of thrombus and thromboembolism. This is achieved by providing a valve orifice 12 with an inner lumen diameter ($d_2$ in FIG. 1A) of a generally cylindrical interior bounded by two generally planar segments proximate pivot guards 14 which are generally perpendicular to the axis of rotation of leaflets 16. In one embodiment, the distance $d_1$ between the lumenal planes of pivot guards 14 is not less than about 85% of diameter $d_2$ shown in FIG. 1A. Diameter $d_2$ is not less than about 85% of tissue annulus diameter $d_3$. Diameter $d_3$ is the diameter to the outer edge of orifice 12 but does not include the outer diameter of rims 20 or 22. These dimensional relationship provide increased lumen area. However, as the relative thickness of the heart valve orifice 12 is reduced, the stiffness of valve orifice 12 decreases. One aspect of the invention includes stiffening the orifice with rims as shown in FIGS. 1, 3, 5, 6, 7, 8, 9, 10, 11, 12, 13, 15, 16 and 17A–C. It is within the contemplation of this invention to use a plurality of such rims or protrusions. The additional stiffness provided by at least one rim supplements any reduction in orifice housing stiffness which otherwise could occur due to the thin section.

Rings 120,130,152,162,250,360,550,574 shown in FIGS. 5, 6, 7, 8, 9, 10, 15 and 16 provide additional stiffness which also allows increased lumen area. The rings 120,130, 152, 162,250,360,550,574 may be channeled beam shapes, such as I, V, U or H configurations, which are known in the art to provide additional stiffness. Rings 120,130,152,162,360, 550,574 extend the width of the suture cuff to provide easier stitching during implantation and help to prevent perivalvular leakage. Another advantage of the retention rings described herein is that they are easily assembled with a heart valve. The attachment rings are well suited for an orifice having a reduced thickness and made of relatively low elastic modulus materials such as CVD pyrolytic carbon. Rings 120,130,152,162,550,574 are adapted for mechanization or automation of the assembly process. Furthermore, rings 120,130,152,162,550,574 allow the suture cuff to rotate relative to the orifice Cuff rotation torque may be controlled by controlling friction between the cuff attachment ring and the orifice body. Friction can be controlled by adjusting the crimping force of rings 120,130, 152,162.

The valves set forth herein may be fabricated with any appropriate biocompatible material. In preferred embodiments, the orifice may be of a pyrolytic carbon-coated graphite or other material which is thromboresistant, durable and of sufficient strength, stiffness and fracture resistance. The orifice may consist of a durable, blood compatible coating or film on a substrate. In one embodiment, the coating or film is diamond-like carbon, and the substrate is a metal. Suitable metal substrates include, but are not limited to, titanium and its alloys.

The present invention provides a mechanical heart valve for a small aortic root which significantly reduces stenosis while maintaining an intra-annular barrier which blocks tissue overgrowth of the valving mechanism and lumen. The invention is applicable and beneficial for any size aortic root and to the mitral position. When implanted in the aortic position, the invention beneficially decreases the work load of the left ventricle. Anticipated patient benefits are increased tolerance to exercise, increased rate of regression of left ventricular hypertrophy, and lower incident rate of congestive heart failure. The embodiments set forth herein provide better hemodynamics by means of a relatively low blood flow mean velocity, thus reducing shear stress and thereby reducing the potential for thrombosis. The relatively low mean velocity is attained by increasing the area of the valve lumen. Low mean velocity also provides a decreased occluder drag, since drag is proportional to the square of velocity, thereby further contributing to an increased effective orifice area. Circumferential protrusions or rims are used for attaching the heart valve housing to a suture cuff. Cuff retention mechanisms set forth herein, including rims or protrusions, and attachment rings, are provided which increase the stiffness of the valve body and which provide rotatable coupling. The protrusions provide stiffness to the valve housing thereby allowing the intra-annular and sub-annular thicknesses of the valve housing to be reduced in order to increase the lumen diameter. The supra-annular portion of the valve is of sufficient thickness to provide strength and stiffness. The various embodiments set forth herein provide increased stiffness by selective placement of the rims; provide increased rim height for improved cuff retention; provide increased rim height to protect the cuff attachment and/or rotation mechanisms placed between the rims; provide a larger tissue impingement barrier; reduced supra-annular height to reduce the likelihood of interference with the coronary ostia.

Although the present invention has been described with reference to preferred embodiments, workers skilled in the art will recognize that changes may be made in form and detail without departing from the spirit and scope of the invention. For example, although this description has been largely directed to an aortic mechanical valve, the techniques are also applicable to mitral mechanical heart valves.

What is claimed is:

1. A heart valve prosthesis for replacing a native valve in a tissue annulus of a heart of a patient, comprising:
    a single piece valve orifice housing providing a lumen therethrough and having an outer circumference, a distal annulus, a distal lip, and a rim integral with the housing and formed from a single piece with the housing, the rim having a rim diameter;
    at least one occluder coupled to the orifice housing movable between an open position and a closed position in which flow through the lumen is substantially blocked;
    a suture cuff coupled to the rim and extending around the outer circumference for attaching the housing to a proximal side of the tissue annulus of the heart; and
    first and second pivot guards in the housing extending beyond the distal lip and having a cylindrical outer surface configured to extend into the tissue annulus and generally conforming to the tissue annulus, the pivot guards providing a pivot axis to the at least one occluder, the pivot axis positioned beyond the distal lip.

2. The prosthesis of claim 1 wherein the a distal lip formed from the single piece with the valve housing is defined in the outer circumference of the housing between the rim and the distal annulus and has a diameter less than the rim diameter, the distal lip configured to extend into the tissue annulus and generally conforming to the tissue annulus whereby the rim and suture cuff do not substantially limit the area of the lumen of the housing, the distal lip having an outer circumference substantially parallel with the cylindrical outer surface of the first and second pivot guards.

3. The prosthesis of claim 2 wherein a diameter of the lumen is greater than about 85% of the diameter of the distal lip.

4. The prosthesis of claim 2 wherein the distal lip and the first and second pivot guards are positioned such that substantially only the distal lip and the first and second pivot guards are configured to extend into a chamber of the heart and a majority of the heart valve prosthesis is configured to reside outside of the chamber.

5. The prosthesis of claim 1 wherein the suture cuff is rotatably coupled to the valve housing.

6. The prosthesis of claim 1 wherein the rim provides stiffness to the valve housing.

7. The prosthesis of claim 1 wherein the valve prosthesis is adapted for acrtic valve replacement.

8. The prosthesis of claim 1 wherein the orifice housing is fabricated from pyrolytic carbon or an alloy of pyrolytic carbon.

9. The prosthesis of claim 1 wherein the valve orifice housing includes a coating or film of a durable and blood compatible material.

10. The prosthesis of claim 1 further comprising:
    a second integral rim extending circumferentially around the valve orifice housing; and
    a circumferential ring generally conforming to the valve orifice housing and between the rims, the ring adapted for clamping onto the suture cuff thereby securing the suture cuff to the valve orifice housing.

11. The prosthesis of claim 1, further comprising:
    a ring coupled to the rim and to the suture cuff thereby securing the suture cuff to the rim.

12. The prosthesis of claim 11, wherein the ring comprises a spring clip.

13. The prosthesis of claim 11, wherein the ring clamps onto the suture cuff.

14. The prosthesis of claim 1 including a second rim integral with the housing and monolithically formed with the housing, the second rim extending around the outer circumference of the housing.

15. The prosthesis of claim 14 wherein the rims have a height h in a radial direction to provide stiffness to the housing.

16. The prosthesis of claim 15 including means for attaching the suture cuff to the valve housing, the means for attaching being positioned between the rims and wherein an outer diameter of the means for attaching is less than outer diameters of the rims.

17. The prosthesis of claim 14 wherein one of the rims is segmented into at least two rim segments to facilitate placement of the suture cuff between the rims.

18. The prosthesis of claim 17 including a continuous ring in the suture cuff to maintain attachment of the suture cuff to the housing.

19. The prosthesis of claim 14 further including a V-shaped groove defined between the rims.

* * * * *